(12) United States Patent
Maeda et al.

(10) Patent No.: US 6,972,011 B2
(45) Date of Patent: Dec. 6, 2005

(54) ULTRA-THIN ABSORBING SHEET BODY, DISPOSABLE ABSORBENT ARTICLE PROVIDED WITH ULTRA-THIN ABSORBING SHEET BODY AND PRODUCTION DEVICE FOR ULTRA-THIN ABSORBING SHEET BODY

(75) Inventors: Satoshi Maeda, Tokushima (JP); Kenji Nakaoka, Tokushima (JP); Kenichi Uchimoto, Osaka (JP); Tadashi Hoshikawa, Tokushima (JP); Masaru Fujioka, Tokushima (JP); Kazuyo Mori, Tokushima (JP)

(73) Assignee: Toyo Eizai Kabushiki Kaisha, Ehime (JP)

( * ) Notice: Subject to any disclaimer, the term of this patent is extended or adjusted under 35 U.S.C. 154(b) by 692 days.

(21) Appl. No.: 10/031,684

(22) PCT Filed: May 22, 2001

(86) PCT No.: PCT/JP01/04259

§ 371 (c)(1),
(2), (4) Date: Jan. 22, 2002

(87) PCT Pub. No.: WO01/89439

PCT Pub. Date: Nov. 29, 2001

(65) Prior Publication Data

US 2002/0115969 A1 Aug. 22, 2002

(30) Foreign Application Priority Data

| May 23, 2000 | (JP) | 2000-151966 |
| Jun. 12, 2000 | (JP) | 2000-175663 |
| Jun. 23, 2000 | (JP) | 2000-189946 |

(51) Int. Cl.[7] .............................................. A61F 31/15
(52) U.S. Cl. .................. 604/385.01; 604/367; 604/382; 602/41
(58) Field of Search ................................ 604/367, 368, 604/370, 382, 385.01; 602/41, 55, 56; 156/219, 229

(56) References Cited

U.S. PATENT DOCUMENTS 4,675,209 A  *  6/1987  Pedigrew ..................... 427/194
4,840,692 A  *  6/1989  Kamstrup-Larsen ........ 156/252

(Continued)

FOREIGN PATENT DOCUMENTS

| EP | 0463716 | 1/1992 |
| EP | 568812 | 11/1993 |

(Continued)

OTHER PUBLICATIONS

CD–ROM of the specification and drawings annexed to the request of Japanese Utility Model Application No. 14111/1992 (Laid–open No. 44524/1993) (Wacoal Corporation), Jun. 15, 1993.

*Primary Examiner*—John J. Calvert
*Assistant Examiner*—Michael G. Bogart
(74) *Attorney, Agent, or Firm*—Jordan and Hamburg LLP

(57) ABSTRACT

In an ultra-thin absorbent sheet member $1a$ in which an absorbent polymer powder 3 is adhered to one surface of a first nonwoven fabric 2 by a hotmelt adhesive such that absorbent polymer powder present areas $2c$ and absorbent polymer powder absent areas $2a$, $2b$ exist; the absorbent polymer powder absent areas are present at opposite widthwise ends ($2a$) of the ultra-thin absorbent sheet member and at least one position ($2b$) between the opposite ends; the absorbent polymer powder 3 is bonded to the first nonwoven fabric 2 by first hotmelt adhesive layers S1 formed on an upper side of the first nonwoven fabric 2 and on a lower side of the absorbent polymer powder 3 and a second hotmelt adhesive layer S2 formed to cover upper sides of the absorbent polymer powder present areas $2c$ and the absorbent polymer powder absent areas $2a$, $2b$; and the first hotmelt adhesive layer S1 and the second hotmelt adhesive layer S2 are both made of an aggregate of linear hotmelt adhesive pieces.

17 Claims, 12 Drawing Sheets

U.S. PATENT DOCUMENTS

| | | | |
|---|---|---|---|
| 5,494,622 A | | 2/1996 | Heath et al. |
| 5,718,913 A | * | 2/1998 | Dhuique-Mayer et al. .. 424/449 |
| 5,797,892 A | * | 8/1998 | Glaug et al. ................. 604/361 |
| 5,830,202 A | * | 11/1998 | Bogdanski et al. ......... 604/378 |
| 5,879,751 A | * | 3/1999 | Bogdanski .................. 427/426 |
| 5,885,681 A | * | 3/1999 | Korpman ..................... 428/68 |
| 6,054,631 A | * | 4/2000 | Gent ........................... 604/367 |
| 6,099,515 A | * | 8/2000 | Sugito ................... 604/385.01 |
| 6,569,137 B2 | * | 5/2003 | Suzuki et al. .......... 604/385.01 |
| 2002/0095127 A1 | * | 7/2002 | Fish et al. .................. 604/368 |
| 2003/0060112 A1 | * | 3/2003 | Rezai et al. ................. 442/340 |

FOREIGN PATENT DOCUMENTS

| | | |
|---|---|---|
| GB | 2252047 | 7/1992 |
| JP | 64-2157 | 3/1989 |
| JP | 11-972 | 1/1999 |
| WO | WO 9503019 | 2/1995 |
| WO | WO 9511654 | 5/1995 |
| WO | WO 9617574 | 6/1996 |

* cited by examiner

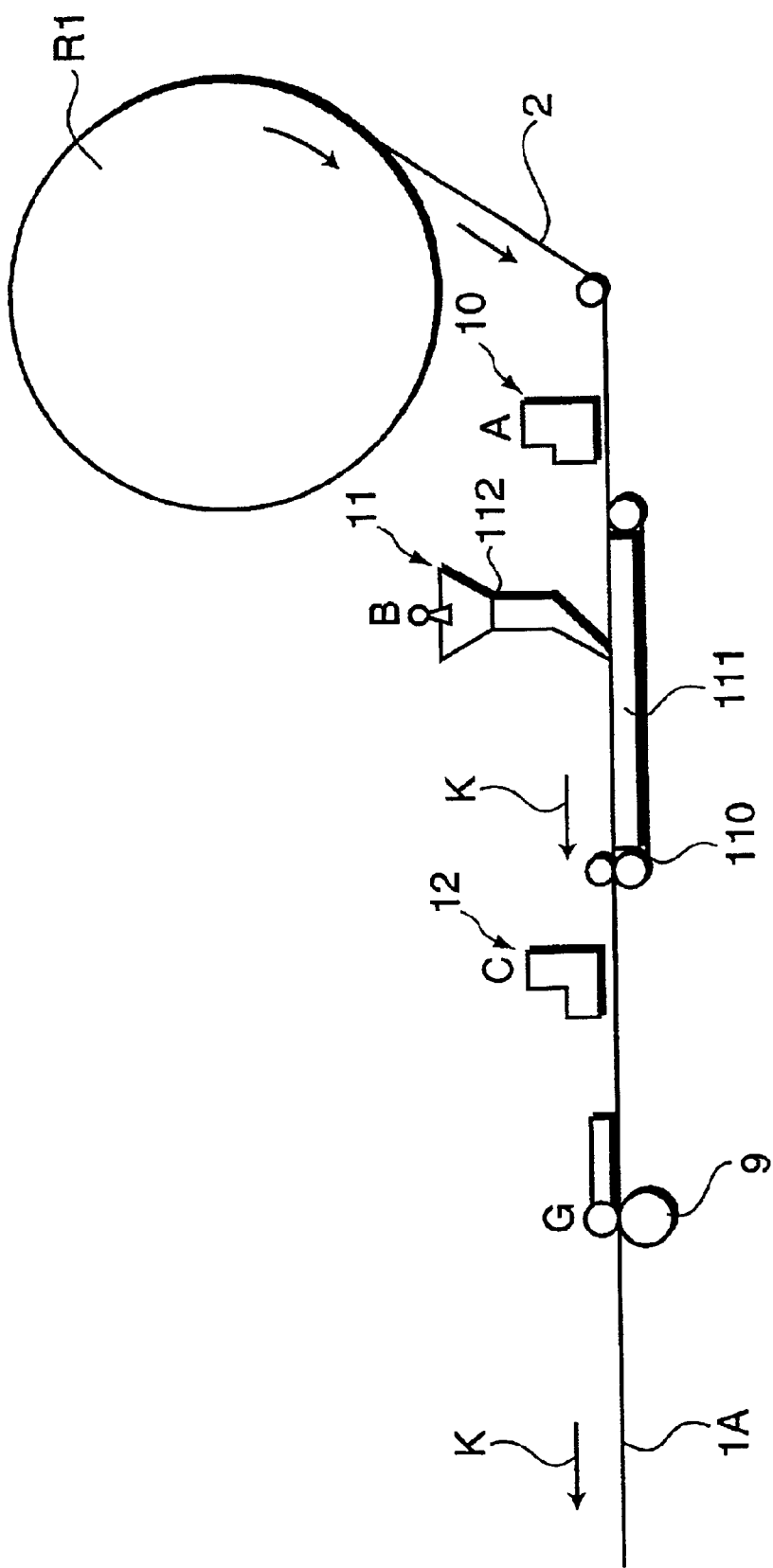

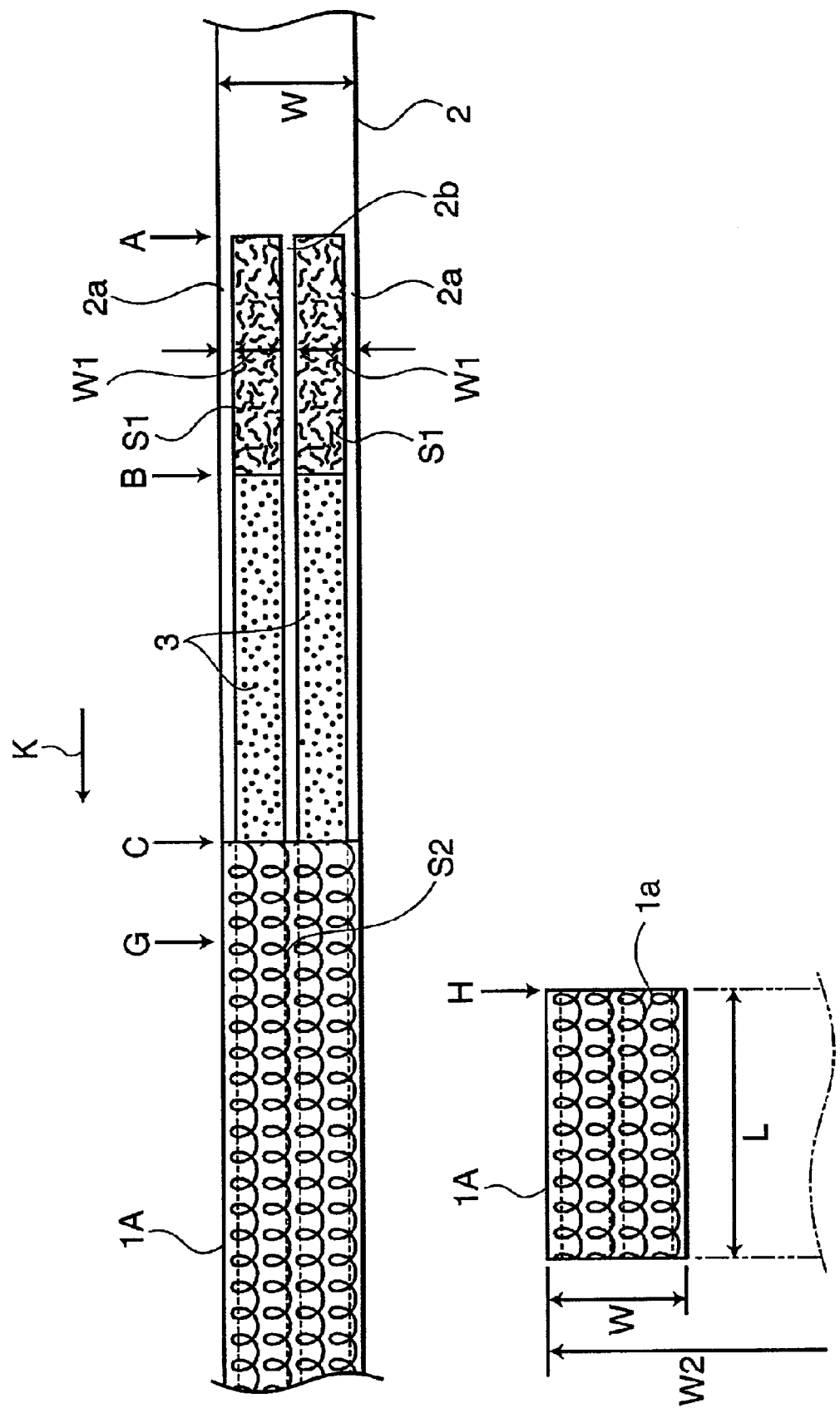

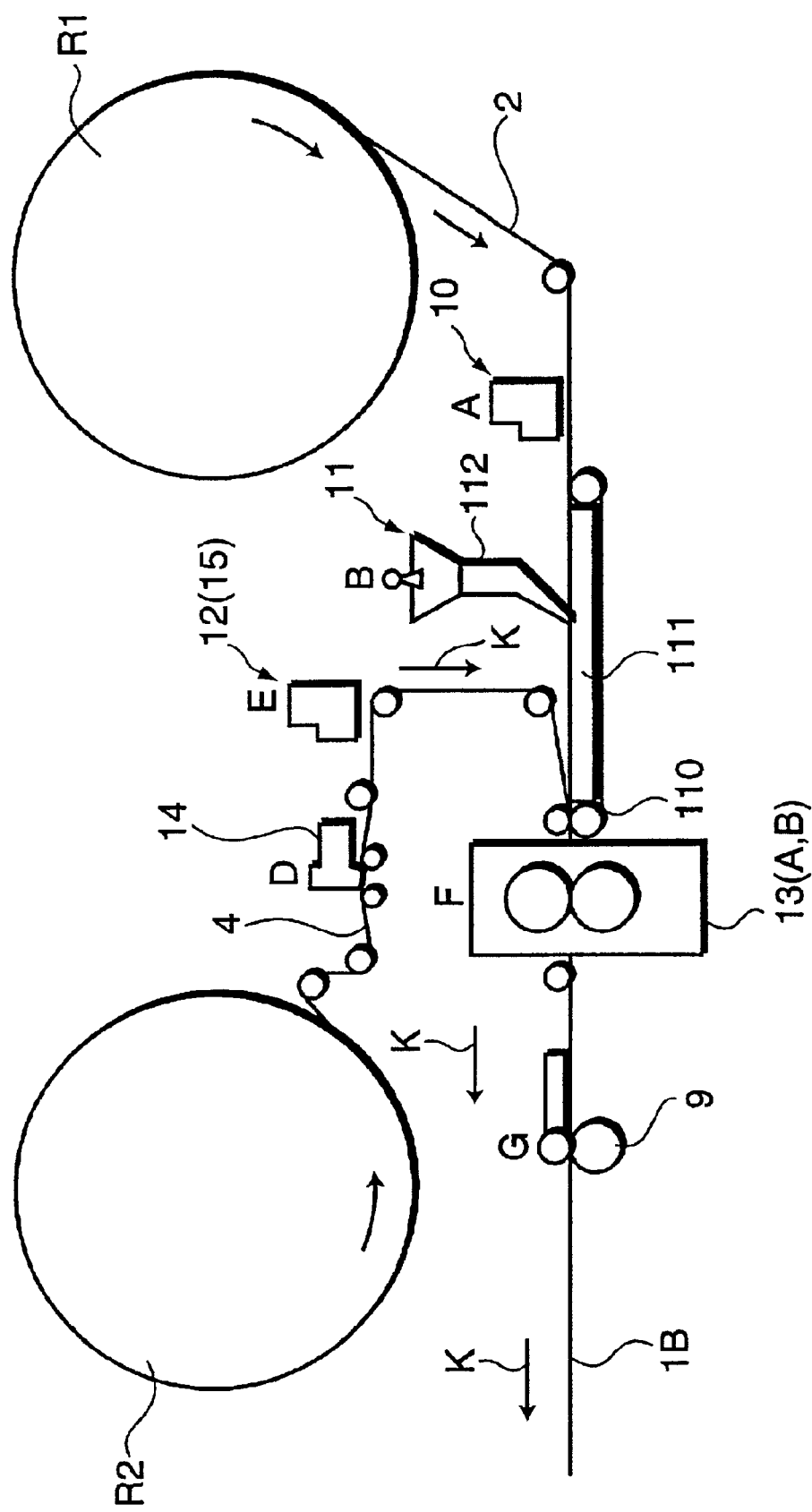

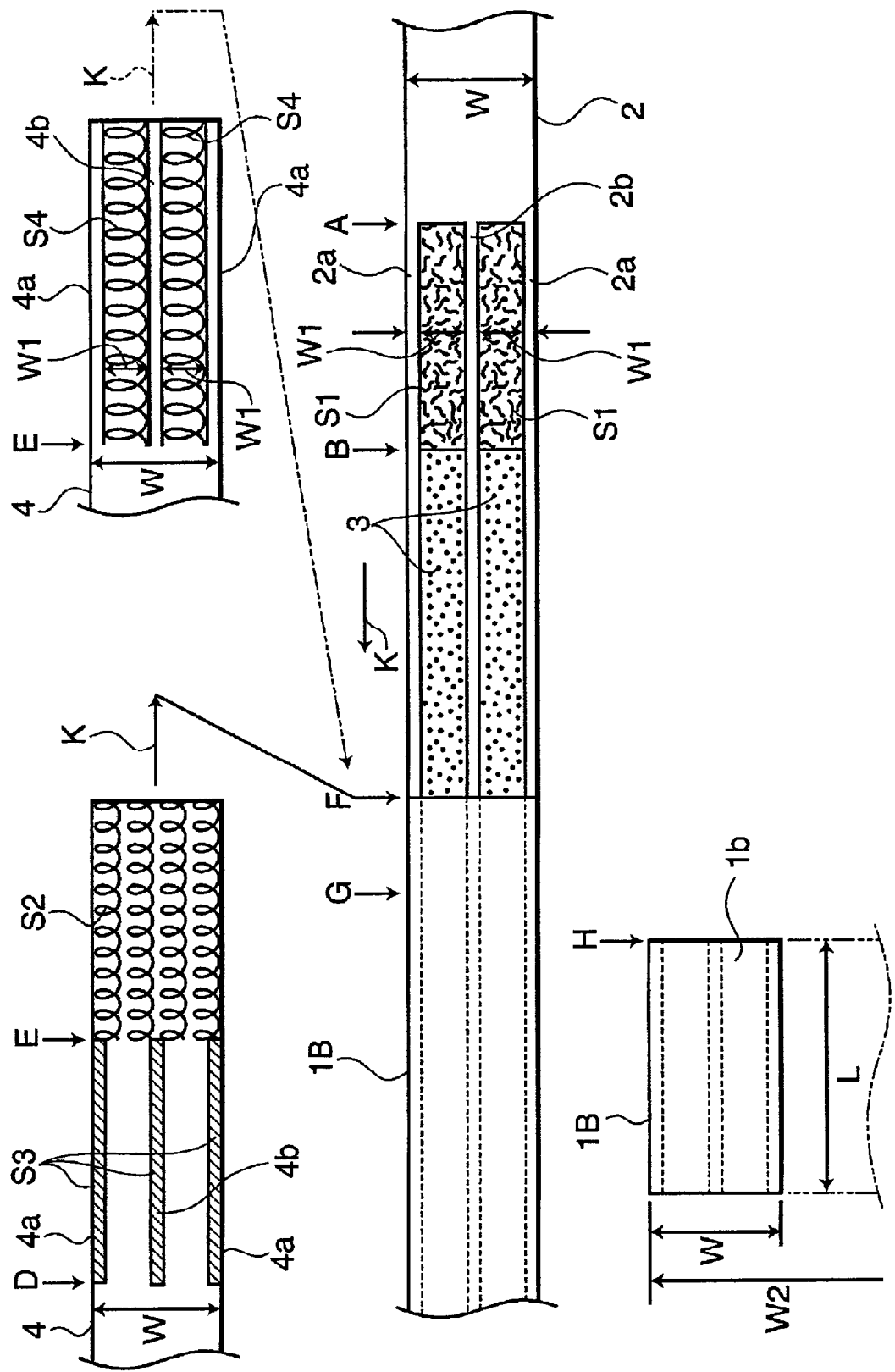

US 6,972,011 B2

ULTRA-THIN ABSORBING SHEET BODY, DISPOSABLE ABSORBENT ARTICLE PROVIDED WITH ULTRA-THIN ABSORBING SHEET BODY AND PRODUCTION DEVICE FOR ULTRA-THIN ABSORBING SHEET BODY

TECHNICAL FIELD

The present invention relates to an ultra-thin absorbent sheet body or member of a sanitary napkin, a disposable diaper, disposable pants or the like for absorbing a body fluid such as uterine flow, urine, and the like, a disposable absorbent article provided with an ultra-thin absorbent sheet member, and an apparatus for producing an ultra-thin absorbent sheet member.

BACKGROUND ART

As an absorbent element has been used an absorbent mat formed by molding a mixture of split yarn pulp fibers, an absorbent polymer powder, thermoplastic fibers and the like into a mat and fixed by covering them with a tissue paper or the like.

However, such an absorbent mat is bulky since it includes pulp fibers and cannot help causing a wearer to feel stiff fitting. Further, the pulp fibers having absorbed the fluid give the wearer an uncomfortable feeling of being "wet". Thus, reduction of an amount of pulp fibers or an absorbent element including no pulp fiber has been considered in order to obtain an absorbent element which is thinner and has a better portability and a more comfortable wear-feeling when being used.

An example of a thin absorbent element including no pulp fiber is constructed such that an absorbent polymer powder is held between two nonwoven fabrics. In order to securely hold the absorbent polymer powder between the nonwoven fabrics, it is a general practice to apply a hotmelt adhesive to the substantially entire surfaces of sheets and to uniformly distribute the absorbent resin substantially over the entire surfaces of the sheets. The thin absorbent element of this type has had a problem that, when a body fluid such as urine is discharged in large quantity at once, the urine leaks from the side surfaces or the like of the absorbent element because absorption by the absorbent resin can not keep up with the leakage.

This is thought to be caused by the following. When an excessive amount of the hotmelt adhesive is used to fix the absorbent polymer, a fairly large part of the outer surface of the absorbed polymer powder is covered by the hotmelt adhesive, with the result that the absorbent resin cannot sufficiently display its absorbing ability. Further, the absorbent polymer powder is hindered from swelling since it is held between the sheets and restricted by the hotmelt adhesive.

In view of the above, a method for applying a small amount of the hotmelt adhesive is being considered instead of applying it to the surface. For example, Japanese Unexamined Patent Publication No. 5-38350 discloses an absorbent article in which sheets and an absorbent polymer powder are bonded by an adhesive applied in dotted lines, straight lines or curved lines. However, even in this invention, the two sheets (absorbent materials) and the absorbent polymer powder are compressed into an integral piece after holding the absorbent polymer powder between the two sheets. Thus, even if the absorbent polymer powder tries to swell upon absorbing the fluid, it cannot sufficiently display its absorbing ability by being restricted by the upper and lower sheets.

A first object of the present invention is to provide an ultra-thin absorbent sheet member which is constructed such that an absorbent polymer powder is securely held and fixed only by one nonwoven fabric, and is not hindered from swelling.

A second object of the present invention is to provide an ultra-thin absorbent sheet member which is constructed such that an absorbent polymer powder is held between two nonwoven fabrics, is not hindered from swelling and is stably fixed to the sheet member.

A third object of the present invention is to provide a disposable absorbent article provided with the above ultra-thin absorbent sheet member.

A fourth object of the present invention is to provide a simple and inexpensive apparatus for inexpensively producing an ultra-thin absorbent sheet member.

DISCLOSURE OF THE INVENTION

An ultra-thin absorbent sheet member of a first embodiment of the present invention which element accomplishes the first object is an ultra-thin absorbent sheet member in which an absorbent polymer powder is adhered to one surface of a first nonwoven fabric by a hotmelt adhesive such that an absorbent polymer powder present area and an absorbent polymer powder absent area exist, wherein the absorbent polymer powder absent area is present at opposite widthwise end portions of the ultra-thin absorbent sheet member and at least one location between the opposite end portions; the absorbent polymer powder is bonded to the first nonwoven fabric by a first hotmelt adhesive layer formed at an upper side of the first nonwoven fabric and at a lower side of the absorbent polymer powder and a second hotmelt adhesive layer formed to cover upper sides of the absorbent polymer powder present area and the absorbent polymer powder absent area; and the first and second hotmelt adhesive layers are both made of an aggregate of linear hotmelt adhesive pieces.

An ultra-thin absorbent sheet member of a second embodiment of the present invention which element accomplishes the second object is an ultra-thin absorbent sheet member in which an absorbent polymer powder is adhered between a first and a second nonwoven fabrics by a first and a second hotmelt adhesive layers such that an absorbent polymer powder present area and an absorbent polymer powder absent area exist, wherein the absorbent polymer powder absent area is present at opposite widthwise end portions of the ultra-thin absorbent sheet member and at least one location between the opposite end portions; the first hotmelt adhesive layer is formed at an upper side of the first nonwoven fabric and at a lower side of the absorbent polymer powder; the second hotmelt adhesive layer is so formed at a lower side of the second nonwoven fabric as to cover at least an upper side of the absorbent polymer powder present area; and the first and second hotmelt adhesive layers are both made of an aggregate of linear hotmelt adhesive pieces.

A disposable absorbent article according to the present invention which article accomplishes the third object is a disposable absorbent article comprising an ultra-thin absorbent sheet member of the first or second embodiment as an absorbent element.

An apparatus for producing the ultra-thin absorbent sheet member according to the first embodiment of the present invention which apparatus accomplished the fourth object is an apparatus for producing an ultra-thin absorbent sheet member, comprising a running device for continuously running a first nonwoven fabric having a specified width in lengthwise direction; a first hotmelt adhesive applicator for continuously applying a first hotmelt adhesive to the upper surface of the running nonwoven fabric except absorbent polymer powder absent areas at opposite widthwise end portions and an absorbent polymer powder absent area located at least at one location between the opposite widthwise end portions while defining clearances; an absorbent polymer powder feeding device for continuously feeding an absorbent polymer powder to the upper surface of the running first nonwoven fabric to adhere the absorbent polymer powder to the first hotmelt adhesive; and a second hotmelt adhesive applicator for continuously applying a second hotmelt adhesive to the upper surface of the running first nonwoven fabric over the entire width while defining clearances.

An apparatus for producing the ultra-thin absorbent sheet member according to the second embodiment of the present invention which apparatus accomplished the fourth object is an apparatus for producing an ultra-thin absorbent sheet member, comprising a running device for continuously running a first nonwoven fabric having a specified width in lengthwise direction; a first hotmelt adhesive applicator for continuously applying a first hotmelt adhesive to the upper surface of the running first nonwoven fabric except absorbent polymer powder absent areas at opposite widthwise end portions and an absorbent polymer powder absent area located at least at one location between the opposite widthwise end portions while defining clearances; an absorbent polymer powder feeding device for continuously feeding an absorbent polymer powder to the upper surface of the running first nonwoven fabric to adhere the absorbent polymer powder to the first hotmelt adhesive; a running device for continuously running a second nonwoven fabric having a specified width in lengthwise direction; a second hotmelt adhesive applicator for continuously applying a second hotmelt adhesive to the upper surface of the running second nonwoven fabric over the entire width while defining clearances; and a bonding device for aligning the upper surface of the running first nonwoven fabric and that of the running second nonwoven fabric with respect to widthwise direction and bonding them in the absorbent polymer powder absent areas at opposite widthwise end portions and in the absorbent polymer powder absent area located at least at one location between the opposite widthwise end portions.

BRIEF DESCRIPTION OF THE DRAWINGS

FIG. 7 is a side view of an apparatus for producing the ultra-thin absorbent sheet member of the first embodiment of the invention, FIG. 9 is a diagram showing a production process of the ultra-thin absorbent sheet member of the first embodiment, FIG. 10 is a side view of an apparatus for producing the ultra-thin absorbent sheet member of the second embodiment of the invention, FIG. 12 is a diagram showing a production process of the ultra-thin absorbent sheet member of the second embodiment.

BEST MODE FOR CARRYING OUT THE INVENTION

Figure 1:
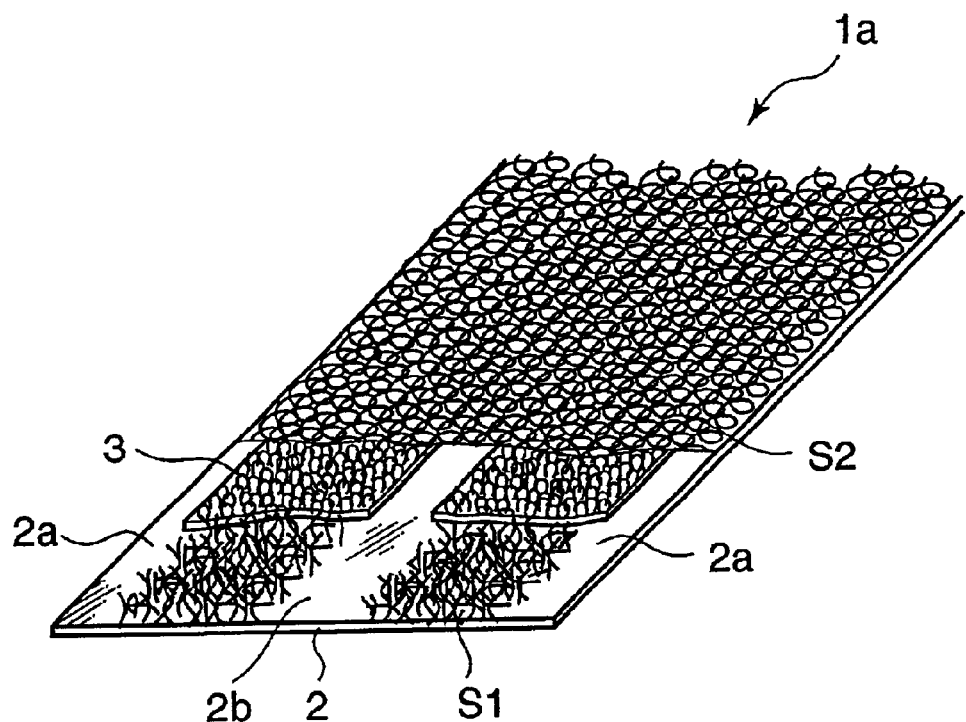
FIG. 1 is a perspective view partly cut away showing an ultra-thin absorbent sheet member according to a first embodiment of the invention.

By adopting a construction of the ultra-thin absorbent sheet member according to the first embodiment of the present invention, an ultra-thin absorbent sheet member in which an absorbent polymer powder is bonded to one side of a nonwoven fabric could be provided. Since not being held between nonwoven fabrics, the absorbent polymer powder can sufficiently display its absorbing ability without being hindered from swelling.

On the other hand, since the ultra-thin absorbent sheet member of the second embodiment of the present invention adopts a construction in which the absorbent polymer powder is bonded and fixed to two nonwoven fabrics, the polymer powder is stably fixed and does not change its position before and after absorption of urine. Thus, there could be provided an ultra-thin absorbent sheet member which has an excellent form stability, does not hinder the absorbent resin from swelling and has an excellent air permeability.

Since the first and second hotmelt adhesives are aggregates of the linear hotmelt adhesive pieces in the ultra-thin absorbent sheet members of both first and second embodiments, the absorbent polymer powder could be securely fixed and held on the nonwoven fabric while ensuring air permeability. Further, since the nonwoven fabric located in the absorbent polymer powder absent areas quickly diffuses the discharged urine or body fluid, the discharged fluid can be quickly diffused in the entire nonwoven fabric, thereby maximally preventing the body fluid or the like from laterally leaking by the succeeding absorption of the absorbent polymer powder. Furthermore, since the swollen absorbent resin does not exist in the absorbent polymer powder absent areas even after the absorption of the body fluid or the like, an air permeability can be ensured, thereby reducing a sweaty feeling given to a wearer.

Both a construction in which the nonwoven fabric has a substantially quadrilateral shape having longitudinal and widthwise directions and the absorbent polymer powder absent areas are strip portions extending in the longitudinal direction of the nonwoven fabric and a construction in which the strip portions are provided in an intermediate area and in opposite widthwise end portions of the nonwoven fabric are preferred embodiments of the present invention. In these preferred embodiments, discharged urine and body fluid can be quickly diffused in the longitudinal direction of the nonwoven fabric. It should be noted that an area ratio of the absorbent polymer powder present area and the absorbent polymer powder absent areas is preferably 1:9 to 5:5, at which ratio the diffusion and absorption characteristic of the body fluid are satisfactorily balanced.

The first hotmelt adhesive layer preferably takes a network structure formed by randomly adhering a large number of fibrillated hotmelt adhesive pieces to each other. This is because the absorbent polymer powder can be securely bonded and fixed while ensuring air permeability.

The second hotmelt adhesive layer is preferably formed by placing a plurality of linear hotmelt adhesive pieces having a spiral contour one over another. Such an adhesive layer has an excellent effect of preventing the absorbent resin from falling off from the nonwoven fabric by holding the absorbent resin fast even when the absorbent resin is swollen. Further, the second hotmelt adhesive layer may be formed by placing a network structure formed by randomly adhering a large number of fibrillated hotmelt adhesive pieces to each other and a plurality of linear hotmelt adhesive pieces having a spiral contour one over another. Such a second hotmelt adhesive layer can more securely hold and fix the absorbent resin. Adhered amounts of the first and second hotmelt adhesive layers are both preferably 1 to 20 g/m$^2$. Within this range, the bonding and fixing force of the absorbent resin and the air permeability are well-balanced. The air permeability of the ultra-thin absorbent sheet member is preferably 6000 cc/m$^2$·24 hrs or higher.

The present invention also embraces disposable absorbent articles provided with the ultra-thin absorbent sheet member of the present invention. Such disposable absorbent articles are provided with a top sheet, a back sheet and an absorbent member provided between these two sheets, use the above ultra-thin absorbent sheet member as the absorbent member and can be constructed such that the ultra-thin absorbent sheet member is placed with the nonwoven fabric thereof faced toward the top sheet or such that the absorbent polymer powder absent areas of the ultra-thin absorbent sheet member and the back sheet are bonded together by heat sealing. Such constructions can cause the absorbent polymer to fully display its absorbing ability and can securely bond the ultra-thin absorbent sheet member and the back sheet.

First, the ultra-thin absorbent sheet member according to the first embodiment of the present invention is described.

Figure 2:
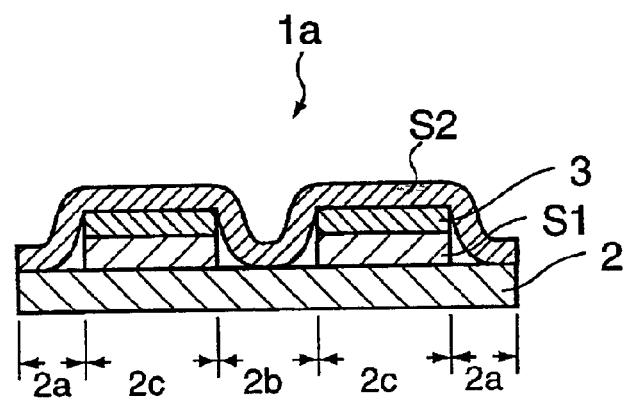
FIG. 2 is a sectional diagram of the ultra-thin absorbent sheet member according to the first embodiment.

FIGS. 1 and 2 are a perspective view partly cut away and a sectional diagram of a typical example of an ultra-thin absorbent sheet member 1a according to the first embodiment of the present invention. The ultra-thin absorbent sheet member 1a is constructed such that first hotmelt adhesive layers S1, S1 are provided at the left and right sides on a first nonwoven fabric 2, absorbent polymer powder layers 3, 3 is provided on each of the left and right first hotmelt adhesive layers S1, S1, and a second hotmelt adhesive layer S2 is further provided substantially over the entire surface of the first nonwoven fabric 2.

Figure 3:
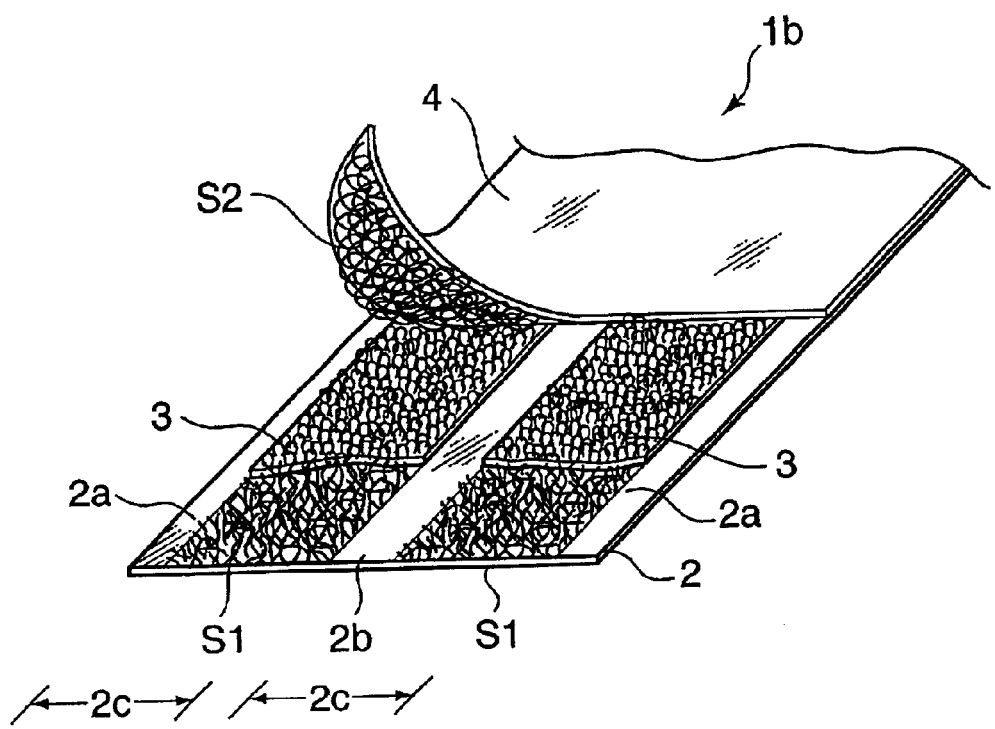
FIG. 3 is a perspective view partly cut away showing an ultra-thin absorbent sheet member according to a second embodiment of the invention.
Figure 4:
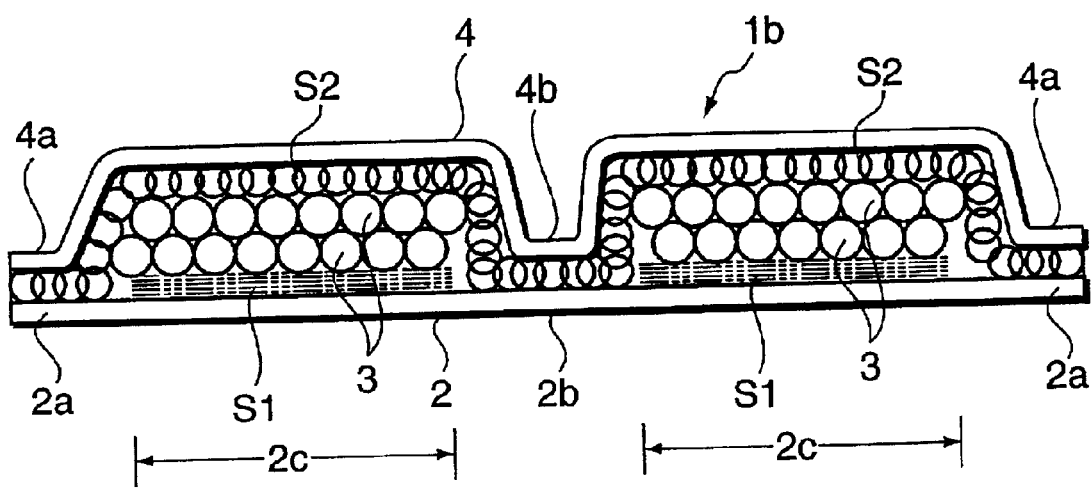
FIG. 4 is a sectional diagram of the ultra-thin absorbent sheet member according to the second embodiment.

On the other hand, FIGS. 3 and 4 are a perspective view partly cut away and a sectional diagram of an ultra-thin absorbent sheet member 1b according to the second embodiment of the present invention. The ultra-thin absorbent sheet member 1b is provided with the first nonwoven fabric 2, the first hotmelt adhesive layers S1, the absorbent polymer powder layers 3 and the second hotmelt adhesive layer S2 which have the same constructions as those of the first embodiment, and is additionally provided with a second nonwoven fabric 4 having substantially the same area and shape as the first nonwoven fabric 2. The second nonwoven fabric 4 is provided on the second hotmelt adhesive layer S2.

Identified by 2a are absorbent polymer powder absent areas at the opposite widthwise end portions (hereinafter, merely opposite end areas 2a), by 2b is an absorbent polymer powder absent area located between the opposite end areas 2a (hereinafter, merely middle area 2b), and by 2c are absorbent polymer powder present areas. Accordingly, the opposite end areas 2a and the middle area 2b are provided as the absorbent polymer powder absent areas in the ultra-thin absorbent sheet member 1a or 1b in the shown example, and the absorbent polymer powder present areas 2c are partitioned into left and right sections by the middle area 2b.

Since the first hotmelt adhesive layers S1 are layers for bonding and fixing the absorbent polymer powder 3 and the first nonwoven fabric 2, they need to be formed in the absorbent polymer powder present areas 2c, 2c. The lateral portions of the first hotmelt adhesive layers S1 may overlap the opposite end areas 2a or the middle area 2b. This is because the first hotmelt adhesive layers are aggregates of the linear hotmelt adhesive pieces and does not hinder air permeability as described later.

On the other hand, the second hotmelt adhesive layer S2 is preferably so formed as to cover or extend over the opposite end areas 2a and the middle area 2b, which are the absorbent polymer powder absent areas, and the absorbent polymer powder present areas 2c. Since the ultra-thin absorbent sheet member 1a does not include the second nonwoven fabric 4 unlike the ultra-thin absorbent sheet member 1b, the absorbent polymer powder 3 needs to be securely fixed to the first nonwoven fabric 2. To this end, the second hotmelt adhesive layer S2 is preferably substantially of the same size as the first nonwoven fabric 2. Since the second hotmelt adhesive layer S2 is also an aggregate of the linear hotmelt adhesive pieces as described later, it does not hinder air permeability.

In the ultra-thin absorbent sheet member 1b of the second embodiment, the absorbent polymer powder 3 can be securely held and fixed between the second nonwoven fabric 4 and the first nonwoven fabric 2 by the second hotmelt adhesive layer S2. In the example shown in FIGS. 3 and 4, the second hotmelt adhesive layer S2 is formed to extend substantially over the entire surface of the first nonwoven fabric 2. Since the second hotmelt adhesive layer S2 is present in the opposite end areas 2a and the middle area 2b in this example, the opposite end areas 2a of the first nonwoven fabric 2 and portions 4a of the second nonwoven fabric 4, the middle area 2b of the first nonwoven fabric 2 and a portion 4b of the second nonwoven fabric 4 are bonded by the second hotmelt adhesive layer S2. If the second hotmelt adhesive layer S2 is applied twice at the opposite end areas 2a and the middle area 2b, the first nonwoven fabric 2 and the second nonwoven fabric 4 can be more strongly bonded.

On the other hand, in the ultra-thin absorbent sheet member 1b of the second embodiment, the second hotmelt adhesive layer S2 may be formed on portions corresponding to the absorbent polymer powder present areas 2c instead of being on the entire surface of the second nonwoven fabric. In other words, the second hotmelt adhesive layer S2 may not be formed in the opposite end areas 2a and the middle area 2b. In such a case, the first hotmelt adhesive layer S1 may be formed over the entire surface of the first nonwoven fabric 2, thereby bonding the first nonwoven fabric 2 and the second nonwoven fabric 4 together. Further, heat sealing may be applied to the first nonwoven fabric 2 and the second nonwoven fabric 4 in the opposite end areas 2a and the middle area 2b where no absorbent polymer powder is present. If heat sealing is applied, the first nonwoven fabric 2 and the second nonwoven fabric 4 can be firmly bonded together. In the case that the absorbent polymer powder absent area is formed at a position other than the opposite end areas 2a and the middle area 2b, it is not necessary to bond the first nonwoven fabric 2 and the second nonwoven fabric 4 in all the absorbent polymer powder absent areas by heat sealing, i.e. it is sufficient to bond them to such a degree that the shape of the ultra-thin absorbent sheet member 1b can be retained. In the case of heat sealing, it is not necessary to form both the first hotmelt adhesive layer S1 and the second hotmelt adhesive layer S2 in the opposite end areas 2a and the middle area 2b. Sealing strength is larger if these adhesive layers S1, S2 are not formed in the aforementioned areas 2a and 2b. However, either one or both of the adhesive layers S1, S2 may be formed.

In the ultra-thin absorbent sheet member 1a of the first embodiment, the absorbent polymer powder 3 can fully display its absorbing ability without being hindered from swelling since being not held between the two nonwoven fabrics, and can be securely fixed to and held by the first nonwoven fabric 2 while ensuring air permeability since the first and second hotmelt adhesive layers S1, S2 are aggregates of the linear hotmelt adhesive pieces. Particularly, since the first nonwoven fabric 2 and the second hotmelt adhesive layer S2 are placed one over the other in the opposite end areas 2a and the middle area 2b, air permeability is good, which causes a wearer to have no sweaty feeling after absorption of the body fluid. Thus, this absorbent sheet member gives the wearer a refreshing wear-feeling.

On the other hand, the ultra-thin absorbent sheet member 1b of the second embodiment is constructed such that the absorbent polymer powder 3 is tightly held between the first nonwoven fabric 2 and the second nonwoven fabric 4 via the first hotmelt adhesive S1 and the second hotmelt adhesive layers S2. Even if a wearer takes a hard exercise, the absorbent polymer powder 3 can be securely fixed and held.

In the ultra-thin absorbent sheet members 1a, 1b of the first and second embodiments, upon the discharge of urine, uterine flow and the like, the absorbent polymer powder absent areas including the opposite end areas 2a and the middle area 2b quickly diffuse these discharged fluids in the entire absorbent polymer powder absent areas 2a, 2b and then diffuse them from the absorbent polymer powder absent areas 2a, 2b to the absorbent polymer powder present areas 2c. Since the fluid absorption of the absorbent polymer powder 3 quickly starts upon the discharge of urine and the like, an inconvenience such as a lateral leak does not occur even if the discharging speed of the discharged fluids exceeds the absorbing speed of the absorbent polymer powder 3 or even if a large amount of body fluid is discharged at once.

A ratio of a total area of the absorbent polymer powder absent areas 2a and 2b to that of the absorbent polymer powder present areas 2c is preferably 1:9 to 5:5. Since the absorbent polymer powder absent areas 2a, 2b play an important role in quickly diffusing urine, uterine flow and the like in the entire ultra-thin absorbent sheet member, there is a possibility of a lateral leak when the body fluid is discharged in large quantity at once and air permeability is poor if the area ratio of the absorbent polymer powder absent areas 2a, 2b is less than 10%. On the other hand, if the area ratio of the absorbent polymer powder absent areas 2a, 2b exceeds 50%, the absorbent polymer powder present areas 2c become smaller, which results in an insufficient absorbing ability. A more preferable area ratio is 2:8 to 4:6.

Although the strip portions extending in the longitudinal direction of the ultra-thin absorbent sheet member 1a or 1b are provided as the absorbent polymer powder absent areas in a total of three areas: the left and right widthwise opposite end areas 2a and the middle area 2b in the examples shown in FIGS. 1 to 4, a plurality of middle areas 2b may be provided. Further, strip portions extending in widthwise directions may be provided as the absorbent polymer powder absent areas, or alternatively strip portions may be set such as those intersected as in a checkerboard instead of extending in the same direction. Other than or in addition to the rectangular strip portions, rhombic or other polygonal strip portions may be provided as the absorbent polymer powder absent areas.

The shape of the first nonwoven fabric 2 and the second nonwoven fabric 4 may be rectangular, square, sandglass-shaped and cocoon-shaped, and may be determined according to application. It is particularly preferable to use substantially quadrilateral nonwoven fabrics having longitudinal and widthwise directions (rectangular, sandglass-shaped, cocoon-shaped). In this case, it is preferable to provided one or more middle areas 2b. By this construction, the discharged urine and uterine flow is quickly diffused in the longitudinal direction of the ultra-thin absorbent sheet member 1a or 1b and absorbed into the absorbent polymer powder 3 while being diffused in widthwise direction, thereby further improving an effect of preventing a lateral leak.

Further, in the case of continuously producing the ultra-thin absorbent sheet members 1a or 1b, a web of the first nonwoven fabrics 2 normally runs in the longitudinal direction of the ultra-thin absorbent sheet members 1a or 1b. Accordingly, if an attempt is made to provide the absorbent polymer powder absent areas extending in widthwise direction, it is necessary to intermittently form the first and second hotmelt adhesive layers S1, S2 and the absorbent polymer powder layers 3 and to synchronize the formation of these layers. Therefore, such absorbent polymer powder absent areas slightly complicate the production process.

On the other hand, in the case of the absorbent polymer powder absent areas extending in longitudinal direction, i.e. in the case of the opposite end areas 2a and the middle area 2b, it is sufficient to use an apparatus to be described later and to adopt a means for forming the first and second hotmelt adhesive layers S1, S2 and the absorbent polymer powder layers 3 only at specified positions, obviating the need for an intermittent operation. This case is preferable since the ultra-thin absorbent sheet members 1a or 1b can be mass-produced at high speed.

The first hotmelt adhesive S1 and the second hotmelt adhesive layers S2 of the ultra-thin absorbent sheet member 1a or 1b according to the present invention are both aggregates of linear (including typical fibrils) hotmelt adhesive pieces. The "aggregate" means the presence of two or more linear hotmelt adhesive pieces. These linear hotmelt adhesive pieces are placed one over another (not necessarily intertwined) while defining clearances. If the hotmelt adhesive is applied over a surface, air permeability is deteriorated, causing a wearer to have a sweaty feeling. However, an aggregate of the linear hotmelt adhesive pieces is applied, the absorbent polymer powder 3 can be securely bonded and fixed to the first nonwoven fabric 2 without deteriorating the air permeability.

Figure 5:
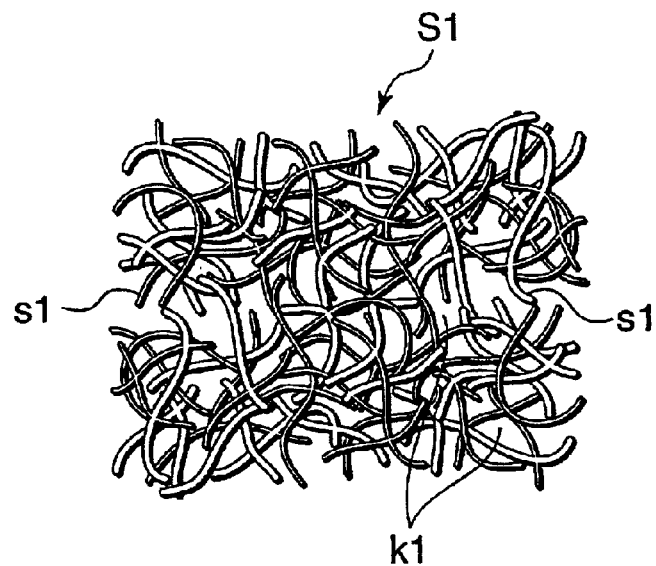
FIG. 5 is an enlarged diagram of an adhesive layer made of fibrillated hotmelt adhesive pieces.

The first hotmelt adhesive layer S1 preferably takes a network structure formed by randomly adhering a large number of fibrillated hotmelt adhesive pieces s1, s1, . . . to each other while defining clearances k1 as in an example of a typical aggregate of fibrils enlargedly and diagrammatically shown in FIG. 5. Such a network structure can be formed by, for example, utilizing a curtain spray coater in which a plurality of small discharge holes are linearly arrayed and air ejection openings capable of ejecting heated air at high speed are provided near the respective discharge holes. With the curtain spray coater, a molten hotmelt adhesive linearly discharged from the discharge holes are narrowly elongated and then broken into fine and short fibrils by being blown at high speed by heated air. Since the hotmelt adhesive pieces discharged from a large number of discharge holes fall onto the outer surface of the running first nonwoven fabric 2 after becoming short fibrils, the network structure in which a large number of fibrillated hotmelt adhesive pieces s1 are randomly adhered to each other is formed on the first nonwoven fabric 2.

An amount of the hotmelt adhesive pieces s1 to be adhered per unit area can be adjusted by adjusting the intervals between the discharge holes of the coater and the running speed of the first nonwoven fabric 2. In view of a good balance of air permeability and a force for bonding the absorbent polymer powder 3, the adhered amount of the first hotmelt adhesive layer S1 is preferably 1 to 20 g/m$^2$. An adhering force for fixing the absorbent polymer powder 3 may be insufficient if the adhered amount is below 1 g/m$^2$.

However, since the adhering force saturates if the adhered amount exceeds 20 g/m$^2$, the hotmelt adhesive pieces are wasted and air permeability is deteriorated. Further, the excessive adhered amount is not preferable since it increases an adhered area of the absorbent polymer powder 3 and the hotmelt adhesive pieces to hinder the absorbent polymer powder 3 from swelling upon absorbing the fluid.

Although the first hotmelt adhesive layers S1 are formed in the absorbent polymer powder present areas 2c, their lateral portions may extend into the absorbent polymer powder absent areas, i.e. into the opposite end areas 2a or the middle area 2b. However, since the second hotmelt adhesive layer S2 is provided on the entire surface of the first nonwoven fabric 2 in the ultra-thin absorbent sheet member 1a, the fluid diffusing effect of the opposite end areas 2a or the middle area 2b may be reduced if the first hotmelt adhesive layers S1 are formed over the entire surface of the first nonwoven fabric 2. Thus, it is preferable that the first hotmelt adhesive layers S1 particularly extend into the middle area 2b only to a small degree. On the other hand, if the second hotmelt adhesive layer S2 is not provided over the entire surface of the second nonwoven fabric 4 in the ultra-thin absorbent sheet member 1b, the first hotmelt adhesive layers S1 may be provided over the entire surface of the first nonwoven fabric 2.

The ultra-thin absorbent sheet member 1a of the present invention is assumed to be used in such a manner that the first nonwoven fabric 2 is on the side in contact with the skin of a wearer. In other words, the absorbent sheet member 1a in its used state is upside down of the state shown in FIG. 1. Since there is a possibility that the absorbent polymer powder 3 is insufficiently fixed only by the first hotmelt adhesive layers S1, the second hotmelt adhesive layer S2 covering the absorbent polymer powder 3 is provided.

Figure 6:
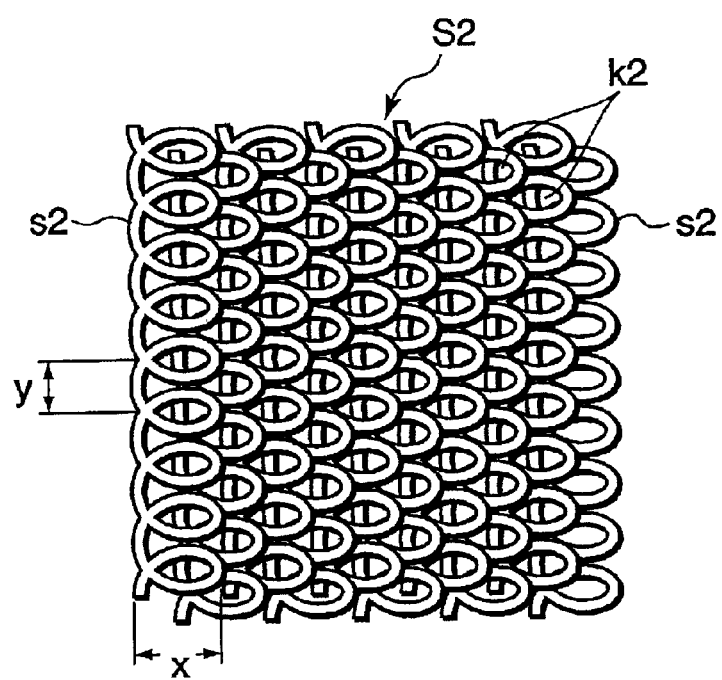
FIG. 6 is an enlarged diagram of an adhesive layer made of linear hotmelt adhesive pieces having a spiral contour.

Similar to the first hotmelt adhesive layers S1, the second hotmelt adhesive layer S2 may take a network structure formed by randomly adhering a large number of fibrillated hotmelt adhesive pieces s1 to each other while defining clearances k1 as shown in FIG. 5. However, the hotmelt adhesive layer S2 is preferably formed by placing a plurality of linear hotmelt adhesive pieces s2, s2, . . . having a spiral contour one over another while defining clearances k2 as shown in FIG. 6. Since the spiral linear hotmelt adhesive pieces s2 are continuous pieces, a network structure stronger than the network structure of the fibrillated hotmelt adhesive pieces s1 formed by the aforementioned curtain spray coater is formed by placing a plurality of these linear hotmelt adhesive pieces s2 one over another, and securely holds and fixes the absorbent polymer powder 3 swollen after absorbing the fluid.

Such spiral linear hotmelt adhesive pieces s2 can be obtained by, for example, a spiral spray gun nozzle in which three or more air ejection openings capable of blowing air in a nozzle center direction are point-symmetrically provided near hotmelt discharge holes. Specifically, a bead of the hotmelt adhesive discharged right below the discharge hole is displaced toward air blown at a certain angle. By blowing air toward the displacement end in a tangential direction of a spiral to be contoured by the hotmelt adhesive, the hotmelt is displaced again. By repeating this displacing operation by a plurality of air ejection openings point-symmetrically provided, the hotmelt adhesive piece falls in spiral shape while maintaining its continuity.

If this linear hotmelt adhesive piece is received onto the stationary nonwoven fabric, it forms a circular contour. However, if this linear hotmelt adhesive is received onto the running nonwoven fabric, it forms a spiral contour. The faster the running speed of the nonwoven fabric, the longer the spiral contour in longitudinal direction. The width x and length y of the spiral contour (see FIG. 6) may be suitably set, but are preferably set at 5 to 30 mm and 5 to 50 mm, respectively.

In the spiral spray nozzle gun, the discharge holes cannot be brought too closer to each other in order to avoid interference of air flows for forming the spiral contour. In the second hotmelt adhesive layer S2 of the present invention, it is preferable to form a strong network structure by placing a plurality of spiral linear hotmelt adhesive pieces s2 one over another. Thus, a plurality of spiral spray nozzle guns may be installed in a production line. By this arrangement, the network structure in which a plurality of spiral hotmelt adhesive pieces s2, s2 . . . are placed one over another as shown in FIG. 6 can be formed. A preferred adhered amount of the second hotmelt adhesive layer S2 made of the spiral linear hotmelt adhesive pieces s2 is 1 to 20 g/m$^2$ for the same reasons described above.

In the ultra-thin absorbent sheet member 1a, the second hotmelt adhesive layer S2 is preferably formed substantially over the entire surface of the first nonwoven fabric 2, because it can then cause the absorbent polymer powder 3 to be securely help by and fixed to the first nonwoven fabric 2. In the ultra-thin absorbent sheet member 1b, the second hotmelt adhesive layer S2 may be formed only in the absorbent polymer powder present areas 2c as described above. Alternatively, the second hotmelt adhesive layer S2 may be so formed as to cover not only the absorbent polymer powder present areas 2c, but also the opposite end areas 2a and the middle area 2b, i.e. to be substantially of the same area as the second nonwoven fabric 4. This is because the spiral hotmelt adhesive pieces s2 does not deteriorate the diffusing ability of the opposite end areas 2a and the middle area 2b which are absorbent polymer powder absent areas since being relatively thick linear pieces.

If the second hotmelt adhesive layer S2 is formed only by the spiral linear hotmelt adhesive pieces s2, the obtained network structure may be wide-meshed. The spiral contour becomes longitudinally long to thereby make the circular portions smaller because of the difficulty in bringing the positions of the discharge holes closer to each other as well as a high running speed of the nonwoven fabric. In view of this, the second hotmelt adhesive layer S2 may take a network structure formed by both the above mentioned spiral linear hotmelt adhesive pieces s2 and the fibrillated hotmelt adhesive pieces s1 obtained by the curtain spray coater. Then, a strong and fine-meshed network structure can be formed. Thus, the absorbent polymer powder 3 can be more securely held and fixed without deteriorating air permeability. A preferred adhered amount of the second hotmelt adhesive layer S2 having this construction is also 1 to 20 g/m$^2$ for the same reasons as described above.

The same kind or different kinds of hotmelt adhesives can be used to form the first and second hotmelt adhesive layers S1, S2, and the kinds thereof are not particularly restricted. In view of productivity, the hotmelt adhesives which melt at about 60 to 180° C. are preferable. For example, styrene elastomers such as SIS (styrene-isoprene-styrene block polymer), SIBS (styrene-isoprene-butadiene-styrene block polymer), SEBS (styrene-ethylene-butylene-styrene block polymer) and SEPS (styrene-ethylene-propylene-styrene block polymer); ethylene-vinyl acetate copolymers; elastomers such as polyester elastomers, acrylic elastomers, polyolefin elastomers or the like; and rubbers such as polyisobutylene, butyl rubber, polyisoprene, natural rubber or the like are preferably used. Materials which can securely fix the absorbent polymer powder 3 swollen after absorbing the fluid and are easily expandable to follow such swollen absorbent polymer powder 3 are preferable. In this respect, styrene elastomers and rubbers are preferable.

The first nonwoven fabric 2 and the second nonwoven fabric 4 may be made of a single nonwoven fabric or take a multi-layer construction in which two or more nonwoven fabrics are placed one over another. In the case of the multi-layer construction, a means for placing the nonwoven fabrics one over another is not particularly restricted, and a known method is used.

The fibers forming the first nonwoven fabric 2 and the second nonwoven fabric 4 may be of the same kind or of different kinds. For example, regenerated fibers such as rayon; polyolefins such as polyethylene and polypropylene; synthetic fibers such as polyester; natural fibers such as silk and pulp (cellulose); and the like are preferably used. Composite fibers such as core-sheath type fibers and side-by-side type fibers may also be used. It is recommended to apply a known hydrophilic treatment (it may be applied after a nonwoven fabric is made) to hydrophobic fibers such as polyolefins.

In the case of applying heat sealing to bond the ultra-thin absorbent sheet member 1a to an other member in the opposite end areas 2a and the middle area 2b or in the case of applying heat sealing to bond the first nonwoven fabric 2 and the second nonwoven fabric 4 in the ultra-thin absorbent sheet member 1b, it is preferable to use nonwoven fabrics containing thermoplastic fibers. Alternatively, a nonwoven fabric containing thermoplastic fibers such as polypropylene or polyethylene may be used at positions where heat sealing is applied. Further, the outermost surface of the first nonwoven fabric 2 and the outermost surface (to be held in contact with the first nonwoven fabric 2) of the second nonwoven fabrics 4 may be made of a nonwoven fabric containing thermoplastic fibers, or such a nonwoven fabric containing thermoplastic fibers may be present only on the outermost surface of the first nonwoven fabric or only on the outermost surface of the second nonwoven fabric.

The fineness of the fibers is not particularly restricted. It may have a general fineness of 1.5 to 4 dtex or fine fibers of 1 dtex or smaller or very thick fibers of 6 dtex or larger may be mixed in order to improve the diffusing ability.

The nonwoven fabric used may be made by any known dry or wet method. A nonwoven fabric formed of rayon fine fibers by a wet method without using any adhesive (e.g. product name "Taiko TCF" produced by Nimura Kagaku Kogyosha) is particularly preferable due to its excellent fluid absorbing ability. The metsuke (weight per m$^2$) of the nonwoven fabric is preferably 10 to 80 g/m$^2$. The nonwoven fabrics whose metsuke lies outside this range are not preferable because they tend to lack strength if the metsuke is below 10 g/m$^2$ while their air permeability gradually decreases if the metsuke exceeds 80 g/m$^2$.

In the case of applying heat sealing to the ultra-thin absorbent sheet member 1a to bond it to an other member in the opposite end areas 2a and the middle area 2b or applying heat sealing to the first nonwoven fabric 2 and the second nonwoven fabric 4 of the ultra-thin absorbent sheet member 1b, a known heat sealing pattern such as an embossing pattern, a checkered pattern or the like may be suitably selected in consideration of a balance between bonding strength and fluid diffusing ability.

Known absorbent resins such as polyacrylate, starch-acrylonitrile resin, cellulose resin or the like can be used as the absorbent polymer powder 3. Absorbent resin having a large water absorption and a high absorbing speed are preferable.

The ultra-thin absorbent sheet member 1a or 1b of the present invention has an air permeability of as high as 6000 cc/m$^2$·24 hrs or higher under conditions B (temperature of 40±0.5° C., relative humidity of 90±2%) specified by JIS Z0208.

The ultra-thin absorbent sheet members 1a of the present invention can be continuously produced using the apparatus to be described later by applying the first hotmelt adhesive S1 to specified positions, feeding the absorbent polymer powder 3 at the specified positions and then applying the second hotmelt adhesive S2 at a specified position while running the first nonwoven fabric 2.

The ultra-thin absorbent sheet members 1b can be continuously produced using the apparatus to be described later by forming the first hotmelt adhesive layers S1 at specified positions, scattering the absorbent polymer powder 3 at specified positions and placing a web of the second nonwoven fabric 4, in which the second hotmelt adhesive layer S2 are formed at a specified position beforehand, such that the second hotmelt adhesive layer S2 is bonded to the absorbent polymer powder present areas 2c while running a web of the first nonwoven fabric 2.

Since the contact of the first hotmelt adhesive layers S1 with the absorbent polymer powder 3 before being cooled and solidified is preferable to increase a bonding force, it is preferable to maximally shorten an interval between the first hotmelt adhesive applying process and the absorbent polymer powder feeding process.

The web of the continuously produced ultra-thin absorbent sheet members 1a or 1b is cut to specified length according to application to become products. In the case that the absorbent polymer powder absent areas are provided in the widthwise direction of the web, the web is preferably cut in these areas. In the case that the absorbent polymer powder absent areas are provided only in the longitudinal direction of the web like the opposite end areas 2a and the middle area 2b, the web may be cut at suitable positions since the cross section thereof along widthwise direction is same at any position. In the case that the first nonwoven fabric 2 and the second nonwoven fabric 4 are made of a plurality of nonwoven fabrics, it is preferable to bond their widthwise ends by bonding means such as heat sealing, ultrasonic fusing or the like before the webs of the nonwoven fabrics are cut by a cutter or like device.

In the case that the ultra-thin absorbent sheet member 1a of the present invention is used by being incorporated as an absorbent member into a disposable absorbent article such as disposable pants, disposable diaper, sanitary pants or the like, it is preferable to incorporate the absorbent sheet member 1a into such a disposable absorbent article with the second hotmelt adhesive layer S2 having a high effect of holding the absorbent polymer powder 3 faced down and the first nonwoven fabric 2 faced toward a wearer's skin between a top sheet and a back sheet. This is because the absorbent polymer powder layers 3 having become heavier after absorbing fluid can be securely held and fixed. For the same reason, the ultra-thin absorbent sheet member 1b is also preferably incorporated into a disposable absorbent article with the second nonwoven fabric 4 faced down and the first nonwoven fabric 2 faced toward a wearer's skin.

Accordingly, the ultra-thin absorbent sheet member 1a or 1b is preferably held between the top sheet (wearer's side sheet) and the back sheet (outer sheet) with the first nonwoven fabric 2 faced toward the top sheet. A diffusing layer made of, e.g. tissues, bulky nonwoven fabric or the like may be provided between the ultra-thin absorbent sheet member 1a or 1b and the top sheet, and a leak preventing material such as an impermeable film or the like may be provided between the ultra-thin absorbent sheet member 1a or 1b and the back sheet. The diffusing layer and the leak preventing material preferably have the same area of the ultra-thin absorbent sheet member 1a or 1b or larger. Further, the diffusing layer may be used as the top sheet and a product such as a disposable pad or the like may be produced by combining this diffusing sheet and the back sheet. Since a construction in which the ultra-thin absorbent sheet member of the present invention is held between the back sheet and the top sheet forms a very thin disposable absorbent article, it is most preferable in view of portability. It should be noted that the disposable absorbent article may be provided with other members known to a person skilled in the art.

Although an impermeable film may also be used as the back sheet, it is preferable to use a permeable film or the like having a good air permeability as such. Further, it is recommended to use a multi-layer back sheet in which an air-permeable, but water-impermeable film having the same area as or a slightly larger area than the ultra-thin absorbent sheet member is placed on a nonwoven fabric (single or multi-layer fabric) and to place the ultra-thin absorbent sheet member and the back sheet one over the other such that the film is in contact with the ultra-thin absorbent sheet member.

By doing so, a disposable absorbent article which is very agreeable to the touch and has excellent external appearance and air permeability can be obtained. It is preferable to use the nonwoven fabric as the top sheet.

In the case of directly bonding the ultra-thin absorbent sheet member 1a of the present invention to the back sheet, the second hotmelt adhesive layer S2 may be utilized. In the case of the ultra-thin absorbent sheet member 1b, a bonding means such as heat sealing or the like may be used. In the case of heat sealing, it is preferable to seal in the absorbent polymer powder absent areas (opposite end areas 2a and middle area 2b). It is not necessary to bond the entire surface of the second nonwoven fabric 4 of the ultra-thin absorbent sheet member 1b to the back sheet for sealing. Sealing may be applied at suitable positions lest the ultra-thin absorbent sheet member 1b should be displaced while the disposable absorbent article is worn. Bonding by an other adhesive may be applied to the absorbent polymer powder absent areas at the lateral sides of the ultra-thin absorbent sheet member.

The present invention also embraces the apparatus for producing the ultra-thin absorbent sheet members 1a and 1b described above. Hereinafter, one embodiment of the inventive apparatus is described in detail with reference to the drawings.

FIGS. 7 to 9, 13 and 14 shows an apparatus for producing a continuous web 1A of the ultra-thin absorbent sheet members 1a of the first embodiment.

As shown in FIG. 7, this producing apparatus is provided with a running device 9 comprised of nip rollers for continuously running the first nonwoven fabric 2 having a specified width W and wound into a roll R1 in lengthwise direction K; a first hotmelt adhesive applicator 10 for continuously applying the first hotmelt adhesive to the upper surface of the running first nonwoven fabric 2 except the opposite end areas 2a and the middle area 2b which are absorbent polymer powder absent areas while defining clearances, an absorbent polymer powder feeding device 11 for continuously feeding the absorbent polymer powder 3 to the upper surface of the running first nonwoven fabric 2 to adhere them to the first hotmelt adhesive layers S1, and a second hotmelt adhesive applicator 12 for continuously applying the second hotmelt adhesive to the upper surface of the running first nonwoven fabric 2 over the entire width W while defining clearances.

Although the width of the web 1A is set at a specified value W in FIG. 9 to facilitate the following description, it may be set at a suitable value according to the number of the ultra-thin absorbent sheet members arrayed in widthwise direction in the case that the ultra-thin absorbent sheet members 1a are simultaneously produced while a plurality of them are arrayed in widthwise direction (described later).

Figure 8A:
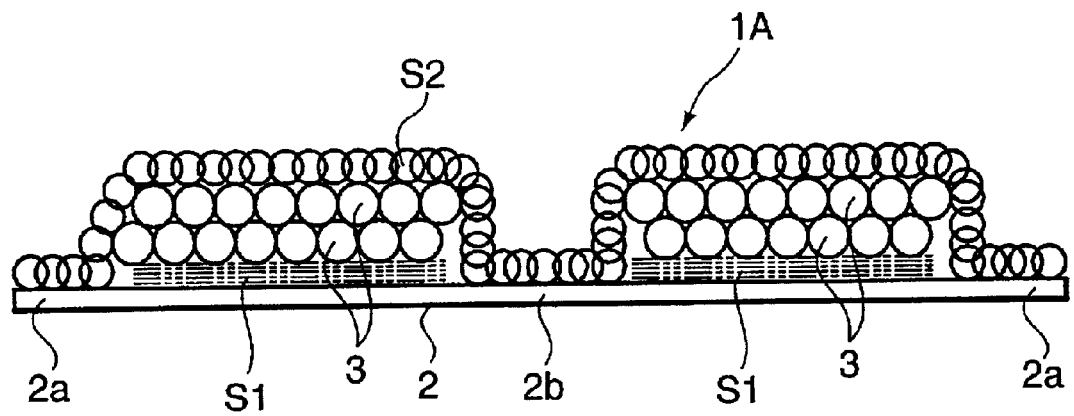
FIG. 8A is a section along widthwise direction of the ultra-thin absorbent sheet member of the first embodiment.
Figure 8B:
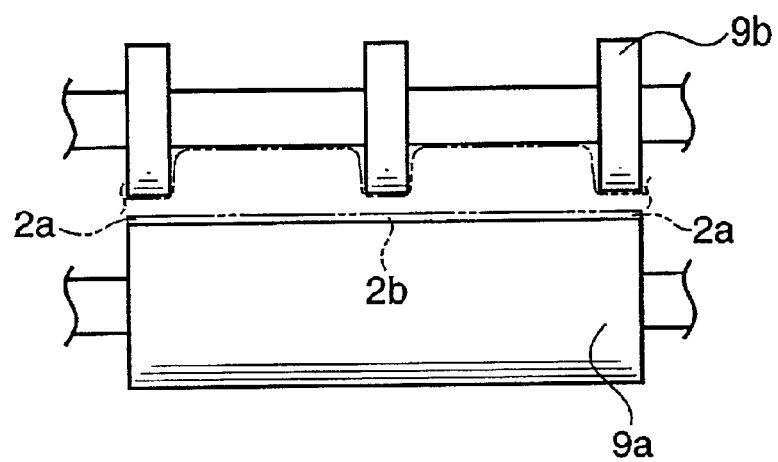
FIG. 8B is a front view of rollers.

The first nonwoven fabric 2 wound into the roll R1 is continuously run at a specified speed in lengthwise direction K by the running device (nip rollers) 9. The running device 9 is comprised of, for example, a metallic flat roller 9a at lower side and a rubber stepped roller 9b at upper side as shown in FIG. 8B, and is adapted to run the web 1A produced to have a cross section along widthwise direction as shown in FIG. 8A while strongly holding the opposite end areas 2a and the middle area 2b of the first nonwoven fabric 2 of the web 1A.

Figure 15A:
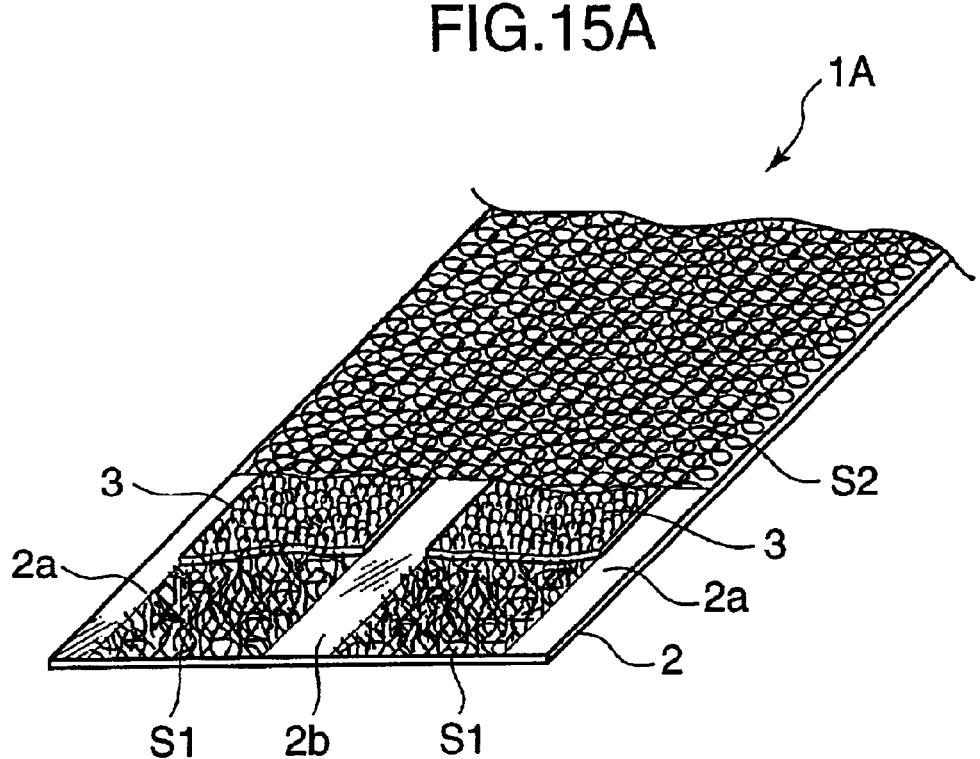
FIG. 15A is a perspective view of the ultra-thin absorbent sheet member of the first embodiment and FIG. 15B is a perspective view of the ultra-thin absorbent sheet member of the second embodiment.

First, the first hotmelt adhesive is continuously applied to the upper surface of the first nonwoven fabric 2 except the opposite end areas 2a and the middle area 2b while defining clearances by means of the first hotmelt adhesive applicator 10 installed at point A, thereby forming the first hotmelt adhesive layers S1 (see A–B of FIG. 9 and FIG. 15A). It should be noted that the absorbent polymer powder absent area corresponding to the middle area 2b is not limited to one position.

An area ratio of the absorbent polymer powder present areas where the first hotmelt adhesive is applied and the absorbent polymer powder absent areas comprised of the opposite end areas 2a and the middle area 2b is preferably 1:9 to 5:5 at which ratio the diffusing ability and the absorption characteristic of the body fluid are satisfactorily balanced, more preferably 2:8 to 4:6.

The first hotmelt adhesive layers S1 are formed by continuously applying the first hotmelt adhesive to the upper surface of the first nonwoven fabric 2 while defining clearances by means of the first hotmelt adhesive applicator 10. As described above, the first hotmelt adhesive layers S1 preferably take such a network structure in which a large number of fibrillated hotmelt adhesive pieces s1 as shown in FIG. 5 are randomly adhered to each other while defining clearances k1.

Subsequently, the absorbent polymer powder 3 is continuously fed to the upper surface of the first nonwoven fabric 2 to be adhered to the first hotmelt adhesive layers S1 by means of the absorbent polymer powder feeding device 11 installed at point B (see B–C of FIG. 9 and FIG. 15A).

Figure 13:
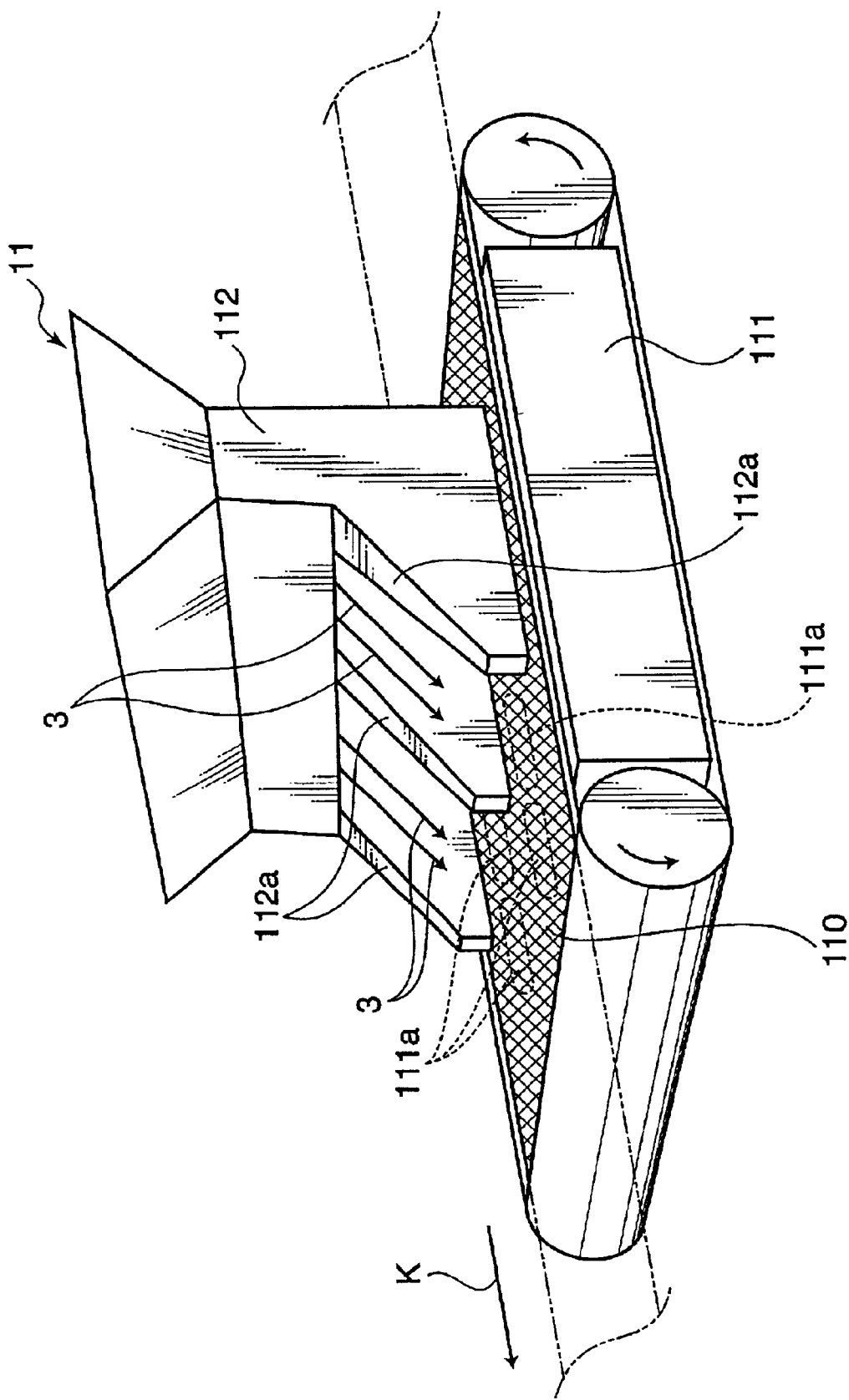
FIG. 13 is a perspective view of an absorbent polymer powder feeding device.
Figure 14A:
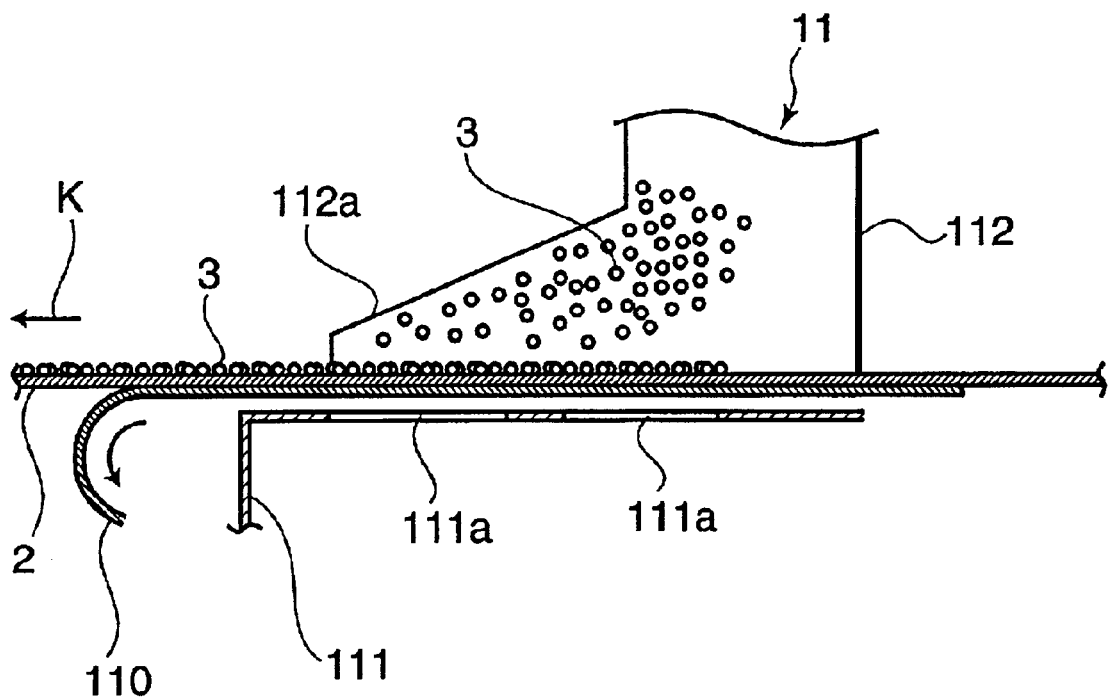
FIGS. 14A and 14B are a side view in section and a front view in section of the absorbent polymer powder feeding device.
Figure 14B:
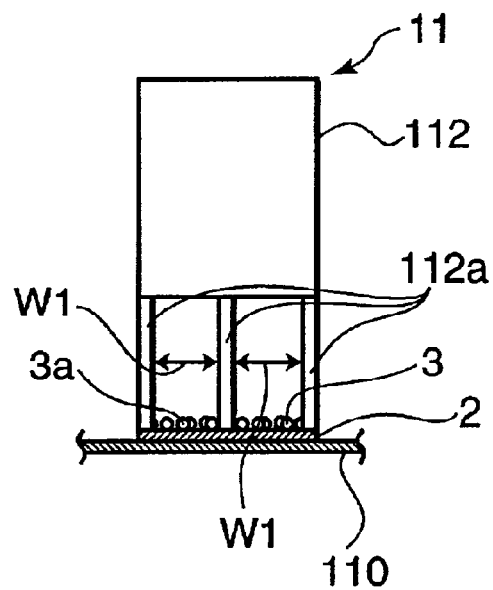

The absorbent polymer powder feeding device 11 is provided with a meshed endless belt 110 which is located at a lower side of the running first nonwoven fabric 2 and is moved at the same speed and in the same direction as the first nonwoven fabric 2 as shown in FIGS. 13 and 14.

A suction box 111 is provided at a lower side of the meshed endless belt 110 and the upper surface of this suction box 111 is formed with suction slits 111a corresponding to width W1 (i.e. spacing between the opposite end areas 2a and the middle area 2b) of the first hotmelt adhesive layers S1 of the first nonwoven fabric 2. Basically, two rows of the suction slits 111a are formed in the widthwise direction of the first nonwoven fabric 2. However, two rows of the suction slits 111a may be formed in forward and backward directions or two rows in widthwise direction may be offset to each other along forward and backward directions.

An absorbent polymer powder feeding hopper 112 is arranged right above the suction box 111 and at an upper side of the first nonwoven fabric 2. Guides 112a corresponding to the width W1 of the first hotmelt adhesive layers S1 of the first nonwoven fabric 2 are formed at a lower part of the absorbent polymer powder feeding hopper 112.

The absorbent polymer powder 3 is fed from the absorbent polymer powder feeding hopper 112 in the respective formation areas of the first hotmelt adhesive layers S1 to have a substantially uniform thickness in synchronism with the running speed of the first nonwoven fabric 2.

Thus, suction forces of the suction slits 111a of the suction box 111 act on the upper surface of the first nonwoven fabric 2 through the meshed belt 110 and the first nonwoven fabric 2. Therefore, the absorbent polymer powder 3 fed from the absorbent polymer powder feeding hopper 112 is adhered to the first hotmelt adhesive layers S1 while being precisely sucked to correspond to the width W1 of the first hotmelt adhesive layers S1 in cooperation with the guides 112a.

The meshed endless belt 110 preferably has a Tyler Standard screen scale of about 200 to 500; the width and length of the suction slits 111a are preferably 5 to 10 mm and 5 to 100 mm, respectively; and an interval between adjacent suction slits 111a is preferably 2 to 5 mm.

Further, the second hotmelt adhesive is continuously applied to the upper surface of the first nonwoven fabric 2 over the entire width W while defining clearances by means of the second hotmelt adhesive applicator 12 installed at point C, thereby forming the second hotmelt adhesive layer S2 (see C–G of FIG. 9 and FIG. 15A).

In this case, the second hotmelt adhesive layer S2 may take a network structure (see FIG. 5) in which a large number of fibrillated hotmelt adhesive pieces s1 are randomly adhered to each other while defining the clearances k1 similar to the first hotmelt adhesive layers S1. However, it is preferable to form such a network structure as enlargedly shown in FIG. 6 in which a plurality of spiral linear hotmelt adhesive pieces s2 are placed one over another while defining clearances k2 as described above.

By installing a curtain spray coater between points B and C or between points C and G in FIG. 7, the fibrillated hotmelt adhesive pieces s1 formed by the curtain spray coater can be added to the bottom or upper side of the spiral linear hotmelt adhesive pieces s2. Since a stronger and finer network structure is formed in this construction, the absorbent polymer powder 3 can be more securely held and fixed without deteriorating air permeability.

The first nonwoven fabric 2 having passed points A to C becomes the web 1A, which is run further in lengthwise direction K by the running device 9 at point G. This web 1A has a cross section along widthwise direction as shown in FIG. 8A.

Figure 8C:
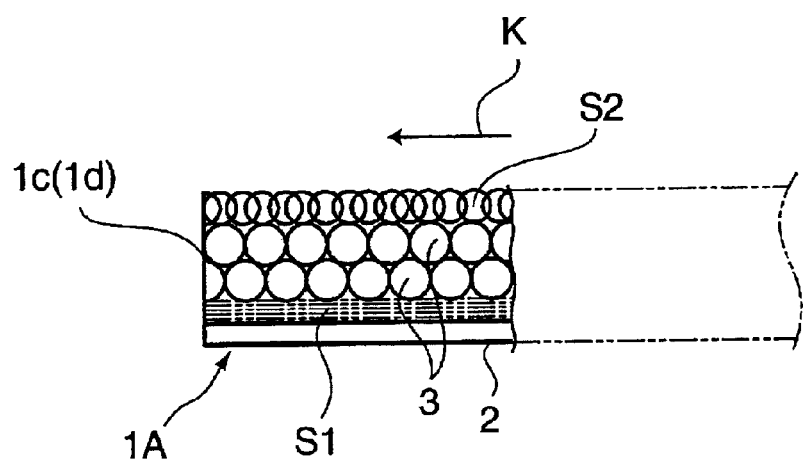
FIG. 8C is a section along longitudinal direction showing an essential portion of the ultra-thin absorbent sheet member of the first embodiment.

Thereafter, the web 1A is stocked by being wound into a roll or cut to specified length L into single piece 1a of the web 1A at point H shown in FIG. 9. A front end 1c and a rear end 1d of the ultra-thin absorbent sheet member 1a obtained by cutting have a cut end as shown in FIG. 8C.

The single piece 1a of the web 1A is preferably used with the first nonwoven fabric 2 faced to be brought into contact with a wearer's skin.

As described above, in the case that a plurality of single pieces 1a are simultaneously formed by being arranged in the widthwise direction of the web 1A, the width of the web 1A may be set at a value W2 corresponding to the number of the single pieces 1a arrayed in the widthwise direction and the web 1A may be cut to specified width W into single pieces 1a.

In the above producing apparatus, since the first hotmelt adhesive is continuously applied to the specified areas (W1) of the first nonwoven fabric 2 to form the first hotmelt adhesive layers S1, the absorbent polymer powder 3 is continuously fed to be adhered to the first hotmelt adhesive layers S1, and then the second hotmelt adhesive is continuously applied to form the second hotmelt adhesive layer S2, no intermittent operation is necessary. This enables a high-speed mass production and, thus, an inexpensive production of the ultra-thin absorbent sheet members 1a. Further, since it is sufficient to provide the running device 9, the first hotmelt adhesive applicator 10, the absorbent polymer powder feeding device 11 and the second hotmelt adhesive applicator 12, the producing apparatus can have a simple construction and can realize lower production costs.

FIGS. 10 to 12 show an apparatus for producing a continues web 1B of the ultra-thin absorbent sheet members 1b of the second embodiment. It should be noted that no detailed description is given on elements having the same construction and functions as the apparatus for producing the web 1A according to the first embodiment by identifying them by the same reference numerals.

As shown in FIG. 10, this producing apparatus is provided with a running device (nip rollers) 9 for continuously running the first nonwoven fabric 2 having a specified width W and wound into a roll R1 in lengthwise direction K; a first hotmelt adhesive applicator 10 for continuously applying the first hotmelt adhesive to the upper surface of the running first nonwoven fabric 2 except the opposite end areas 2a and the middle area 2b while defining clearances to thereby form the first hotmelt adhesive layers S1, an absorbent polymer powder feeding device 11 for continuously feeding the absorbent polymer powder 3 to the upper surface of the running first nonwoven fabric 2 to adhere them to the first hotmelt adhesive layers S1, another running device (nip rollers) 9 for continuously running the second nonwoven fabric 4 having the specified width W and wound into a roll R2 in lengthwise direction K, a second hotmelt adhesive applicator 12 for continuously applying the second hotmelt adhesive to the upper surface of the running second nonwoven fabric 4 over the entire width W while defining clearances to thereby form the second hotmelt adhesive layer S2, and a bonding device 13 for aligning the upper surface of the running first nonwoven fabric 2 and that of the second nonwoven fabric 4 with respect to widthwise direction and bonding them.

The first nonwoven fabric 2 wound into the roll R1 is continuously run at a specified speed in lengthwise direction K by the running device (nip rollers) 9.

Figure 15B:
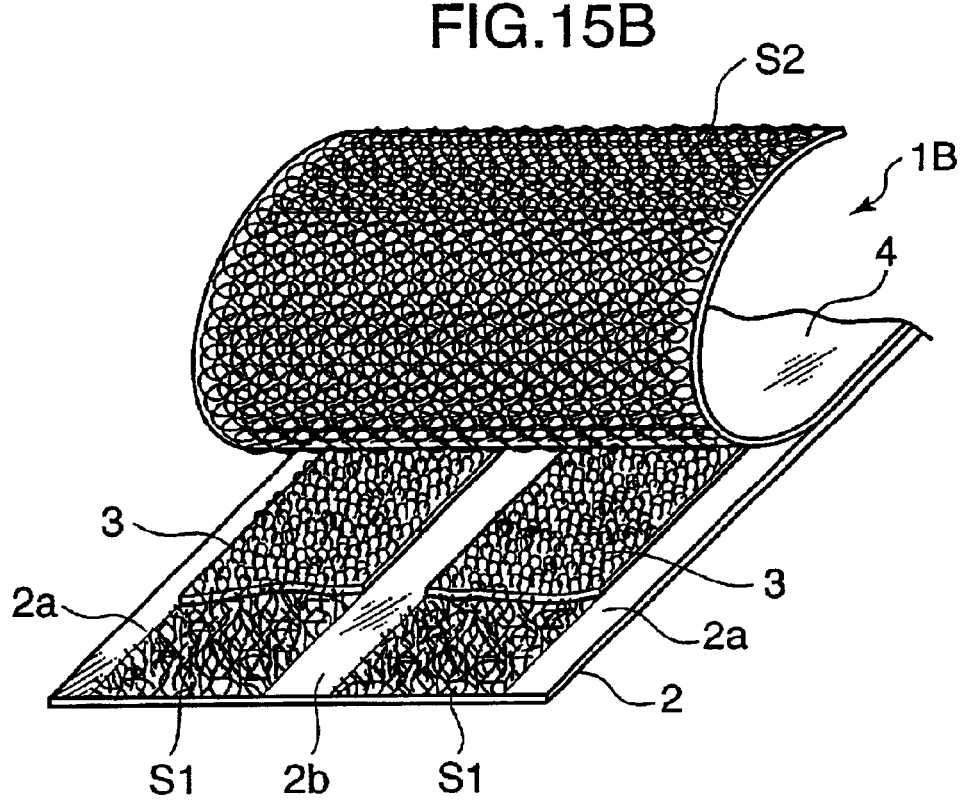

First, the first hotmelt adhesive is continuously applied to the upper surface of the first nonwoven fabric 2 except the opposite end areas 2a and the middle area 2b while defining clearances by means of the first hotmelt adhesive applicator 10 installed at point A, thereby forming the first hotmelt adhesive layers S1 (see A–B of FIG. 12 and FIG. 15B).

Subsequently, the absorbent polymer powder 3 is continuously fed to the upper surface of the first nonwoven fabric 2 to be adhered to the first hotmelt adhesive layers S1 by means of the absorbent polymer powder feeding device 11 installed at point B (see B–F of FIG. 12 and FIG. 15B).

On the other hand, the second nonwoven fabric 4 wound into the roll R2 is continuously run at the specified speed in lengthwise direction K by the running device (nip rollers) 9.

Further, the second hotmelt adhesive is continuously applied to the upper surface of the second nonwoven fabric 4 over the entire width W while defining clearances by means of the second hotmelt adhesive applicator 12 installed at point E, thereby forming the second hotmelt adhesive layer S2 (see E–F of FIG. 12 and FIG. 15B).

If a fourth hotmelt adhesive is continuously applied to the opposite end areas 2a and the middle area 2b of the upper surface of the second nonwoven fabric 4 while defining clearances to form fourth hotmelt adhesive layers S3 by means of a fourth hotmelt adhesive applicator 14 installed at point D which is a previous stage of point E, the opposite end areas 2a, 2a and the middle areas 2b, 2b of the first nonwoven fabric 2 and the second nonwoven fabric 4 can be securely bonded to each other by the bonding device 13A.

Figure 11A:
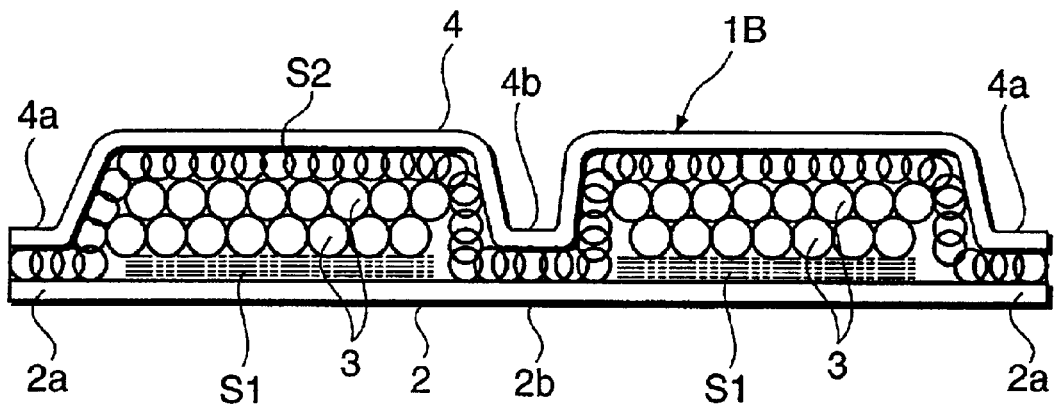
FIG. 11A is a section along widthwise direction of the ultra-thin absorbent sheet member of the second embodiment.

Thereafter, the upper surface of the first nonwoven fabric 2 and that of the second nonwoven fabric 4 are aligned with respect to widthwise direction and bonded to each other by pressing by means of the bonding device 13A installed at point F. Similar to the flat roller 9a and the stepped roller 9b of the running device 9, the bonding device 13A (see FIG. 11B) is comprised of a metallic flat roller 13a at lower side and a metallic stepped roller 13b at upper side, and firmly press-bond the opposite end areas 2a, 2a and the middle areas 2b, 2b of the first and second nonwoven fabrics 2, 4 to each other by suitably pressing the opposite end areas 2a, 2a and the middle areas 2b, 2b of the first nonwoven fabric 2 and the second nonwoven fabric 4 of the web 1B produced to have a cross section along widthwise direction as shown in FIG. 11A.

The first nonwoven fabric 2 and the second nonwoven fabric 4 having passed points A, B, D, E and F become the web 1B, which is run further in lengthwise direction K by the running device 9 at point G. This web 1B has a cross section along widthwise direction as shown in FIG. 11A.

Thereafter, the web 1B is stocked by being wound into a roll or cut to specified length L into single pieces 1b of the web 1B at point H shown in FIG. 12. A front end 1c and a rear end 1d of the ultra-thin absorbent sheet member 1b obtained by cutting have a cut end as shown in FIG. 11C.

The single piece 1b of the web 1B can be used with either one of the first and second nonwoven fabrics 2, 4 faced to be brought into contact with a wearer's skin. However, it is preferable to use it with the first nonwoven fabric 2 faced to be brought into contact with a wearer's skin.

In the above production process, since the first hotmelt adhesive is continuously applied to the specified areas (W1) of the first nonwoven fabric 2 to form the first hotmelt adhesive layers S1, the absorbent polymer powder 3 is continuously fed to be adhered to the first hotmelt adhesive layers S1, the second hotmelt adhesive is continuously applied to the second nonwoven fabric 4 to form the second hotmelt adhesive layer S2, and then the first nonwoven fabric 2 and the second nonwoven fabric 4 are press-bonded, no intermittent operation is necessary. This enables a high-speed mass production and, thus, an inexpensive production of the web 1B. Further, since it is sufficient to provide the running device 9, the first hotmelt adhesive applicator 10, the absorbent polymer powder feeding device 11, the second hotmelt adhesive applicator 12 and the bonding device 13A, the producing apparatus can have a simple construction and can realize lower production costs.

As shown at an upper right part of FIG. 12, similar to the case of forming the second hotmelt adhesive layer S2, third linear hotmelt adhesive pieces having a spiral contour may be continuously applied to the second nonwoven fabric 4 except the opposite end areas 2a and the middle area 2b, similar to the formation of the first hotmelt adhesive layers S1, to form third hotmelt adhesive layers S4 by means of a third hotmelt adhesive applicator 15 instead of the second hotmelt adhesive applicator 12, and the upper surface of the first nonwoven fabric 2 and that of the second nonwoven fabric 4 are aligned with respect to widthwise direction and bonded by heat sealing at the opposite end areas 2a and the middle area 2b by means of a bonding device (heat sealing device) 13B which is installed at point F and is capable of applying heat sealing.

Figure 11B:
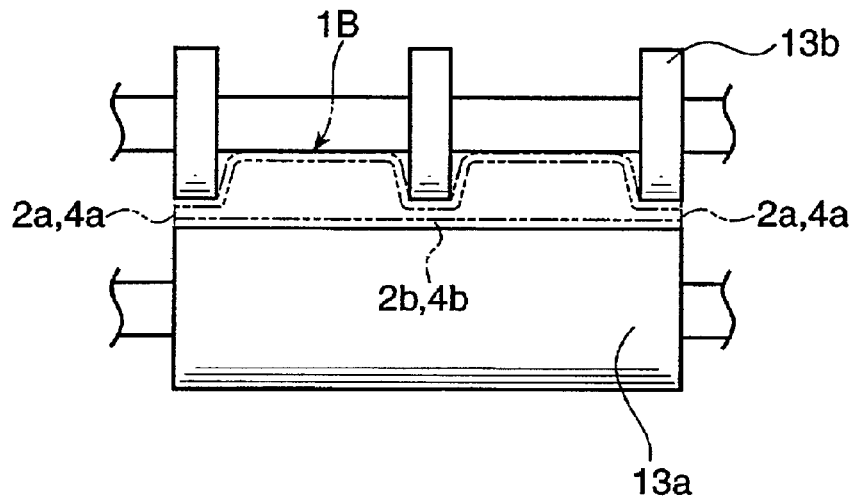
FIG. 11B is a front view of rollers.
Figure 11C:
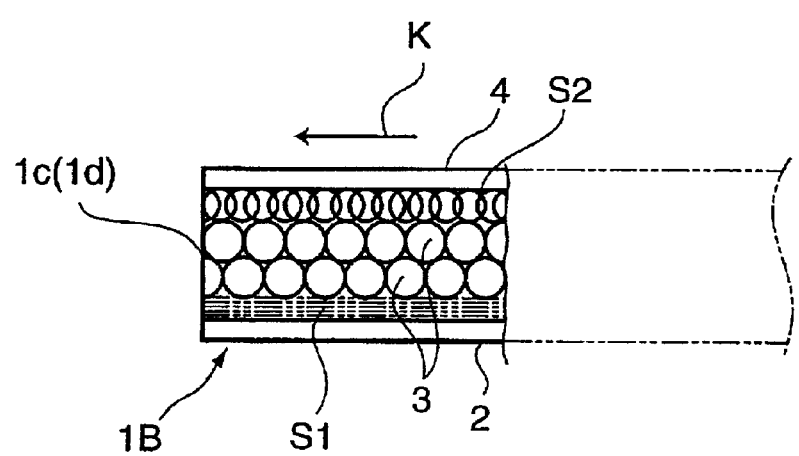
FIG. 11C is a section along longitudinal direction showing an essential portion of the ultra-thin absorbent sheet member of the second embodiment.

The heat sealing device 13B may take the same construction as the bonding device 13A shown in FIG. 11B. Such a device can securely heat-seal the opposite end areas 2a, 2a and the middle areas 2b, 2b of the first nonwoven fabric 2 and the second nonwoven fabric 4 of the web 1B produced to have the cross section along widthwise direction as shown in FIG. 11A, thereby increasing heat-seal strength of the opposite end areas 2a, 2a and the middle areas 2b, 2b of the first nonwoven fabric 2 and the second nonwoven fabric 4.

INDUSTRIAL APPLICABILITY

The present invention could provide an absorbent sheet member which is thin and has an excellent absorbing ability and a producing apparatus having a simple construction. Thus, by using the ultra-thin absorbent sheet member as an absorbent element of disposable pants, a disposable diaper, a urine absorbing auxiliary pad, sanitary pants, pants for light incontinence or the like, a disposable absorbent article which is thin and good in external appearance and does not cause a lateral leak or like inconvenience could be provided. It should be noted that the inventive ultra-thin absorbent sheet member can be applied to agricultural water retaining/absorbing materials, concrete curing mats, condensation preventing sheets, poultices, adhering materials, cosmetic materials, etc. as well as the field of sanitary materials.

What is claimed is:

1. An ultra-thin absorbent sheet member in which an absorbent polymer powder is adhered to one surface of a first nonwoven fabric by a hotmelt adhesive such that an absorbent polymer powder present area and an absorbent polymer powder absent area exist, wherein:

the absorbent polymer powder absent area is present at opposite widthwise end portions of the ultra-thin absorbent sheet member and at least one location between the opposite end portions;

the absorbent polymer powder is bonded to the first nonwoven fabric by a first hotmelt adhesive layer formed at an upper side of the first nonwoven fabric and at a lower side of the absorbent polymer powder and a second hotmelt adhesive layer formed to cover upper sides of the absorbent polymer powder present area and the absorbent polymer powder absent area, and the first and second hotmelt adhesive layers are both made of an aggregate of linear hotmelt adhesive pieces.

2. An ultra-thin absorbent sheet member according to claim 1, wherein the first nonwoven fabric has a substantially quadrilateral shape having longitudinal and widthwise directions, and the absorbent polymer powder absent area is a strip portion extending in the longitudinal direction of the first nonwoven fabric.

3. An ultra-thin absorbent sheet member in which an absorbent polymer powder is adhered between a first and a second nonwoven fabrics by a first and a second hotmelt adhesive layers such that an absorbent polymer powder present area and an absorbent polymer powder absent area exist, wherein:

the absorbent polymer powder absent area is present at opposite widthwise end portions of the ultra-thin absorbent sheet member and at least one location between the opposite end portions, the first hotmelt adhesive layer is formed at an upper side of the first nonwoven fabric and at a lower side of the absorbent polymer powder, the second hotmelt adhesive layer is so formed at a lower side of the second nonwoven fabric as to cover at least an upper side of the absorbent polymer powder present area, and the first and second hotmelt adhesive layers are both made of an aggregate of linear hotmelt adhesive pieces.

4. An ultra-thin absorbent sheet member according to claim 3, wherein the second hotmelt adhesive layer is formed at the lower side of the second nonwoven fabric substantially over the entire surface of the second nonwoven fabric.

5. An ultra-thin absorbent sheet member according to claim 3 or 4, wherein the first and second nonwoven fabrics are formed by a nonwoven fabric containing thermoplastic fibers and are bonded to each other in the absorbent polymer powder absent areas by heat sealing.

6. An ultra-thin absorbent sheet member according to any of claims 1 to 4, wherein an area ratio of the absorbent polymer powder present area and the absorbent polymer powder present area is 1:9 to 5:5.

7. An ultra-thin absorbent sheet member according to any of claims 1 to 4, wherein the first hotmelt adhesive layer takes a network structure formed by randomly adhering a large number of fibrillated hotmelt adhesive pieces to each other.

8. An ultra-thin absorbent sheet member according to any of claims 1 to 4, wherein the second hotmelt adhesive layer is formed by placing a plurality of linear hotmelt adhesive pieces having a spiral contour one over another.

9. An ultra-thin absorbent sheet member according to any of claims 1 to 4, wherein the second hotmelt adhesive layer is formed by placing a network structure formed by randomly adhering a large number of fibrillated hotmelt adhesive pieces to each other and a plurality of linear hotmelt adhesive pieces having a spiral contour one over the other.

10. An ultra-thin absorbent sheet member according to any of claims 1 to 4, wherein adhered amounts of the first and second hotmelt adhesive layers are both 1 to 20 g/m$^2$.

11. An ultra-thin absorbent sheet member according to any of claims 1 to 4, wherein air permeability is 6000 cc/m$^2$·24 hrs.

12. A disposable absorbent article, comprising an ultra-thin absorbent sheet member according to claim 1 as an absorbent element.

13. A disposable absorbent article, comprising an ultra-thin absorbent sheet member according to claim 3 as an absorbent element.

14. An apparatus for producing an ultra-thin absorbent sheet member, comprising:

a running device for continuously running a first nonwoven fabric having a specified width in lengthwise direction, a first hotmelt adhesive applicator for continuously applying a first hotmelt adhesive to the upper surface of the running nonwoven fabric except absorbent polymer powder absent areas at opposite widthwise end portions and an absorbent polymer powder absent area located at least at one location between the opposite widthwise end portions while defining clearances, an absorbent polymer powder feeding device for continuously feeding an absorbent polymer powder to the upper surface of the running first nonwoven fabric to adhere the absorbent polymer powder to the first hotmelt adhesive, and a second hotmelt adhesive applicator for continuously applying a second hotmelt adhesive to the upper surface of the running first nonwoven fabric over the entire width while defining clearances.

15. An apparatus for producing an ultra-thin absorbent sheet member, comprising:

a running device for continuously running a first nonwoven fabric having a specified width in lengthwise direction, a first hotmelt adhesive applicator for continuously applying a first hotmelt adhesive to the upper surface of the running first nonwoven fabric except absorbent polymer powder absent areas at opposite widthwise end portions and an absorbent polymer powder absent area located at least at one location between the opposite widthwise end portions while defining clearances, an absorbent polymer powder feeding device for continuously feeding an absorbent polymer powder to the upper surface of the running first nonwoven fabric to adhere the absorbent polymer powder to the first hotmelt adhesive, a running device for continuously running a second nonwoven fabric having a specified width in lengthwise direction, a second hotmelt adhesive applicator for continuously applying a second hotmelt adhesive to the upper surface of the running second nonwoven fabric over the entire width while defining clearances, and a bonding device for aligning the upper surface of the running first nonwoven fabric and that of the running second nonwoven fabric with respect to widthwise direction and bonding them in the absorbent polymer powder absent areas at opposite widthwise end portions and in the absorbent polymer powder absent area located at least at one location between the opposite widthwise end portions.

16. An apparatus according to claim 15, comprising a third hotmelt adhesive applicator instead of the second hotmelt adhesive applicator for continuously applying a third hotmelt adhesive to the upper surface of the running second nonwoven fabric except absorbent polymer powder absent areas at opposite widthwise end portions and an absorbent polymer powder absent area located at least at one location between the opposite widthwise end portions while defining clearances.

17. An apparatus according to any of claims 13 to 16, wherein the absorbent polymer powder feeding device includes:

a meshed belt located at a lower side of the first nonwoven fabric and moving at the same speed and in the same direction as the first nonwoven fabric, a suction box located at a lower side of the meshed belt and formed with suction slits corresponding to the widths of the respective application areas of the first hotmelt adhesive, and an absorbent polymer powder feeding hopper located at an upper side of the first nonwoven fabric and formed with guides corresponding to the widths of the respective application areas of the first hotmelt adhesive.

* * * * *